United States Patent
Hyde

(10) Patent No.: US 6,945,978 B1
(45) Date of Patent: Sep. 20, 2005

(54) HEART VALVE CATHETER

(75) Inventor: Gregory Matthew Hyde, Menlo Park, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 0 days.

(21) Appl. No.: 10/295,071

(22) Filed: Nov. 15, 2002

(51) Int. Cl.$^7$ ............................. A61B 17/00; A61F 2/24
(52) U.S. Cl. ...................... 606/142; 606/147; 623/2.11
(58) Field of Search ............................ 623/2.11; 606/1, 606/148, 167, 213, 37, 139–147; 128/898

(56) References Cited

U.S. PATENT DOCUMENTS

| | | | |
|---|---|---|---|
| 4,781,186 A | 11/1988 | Simpson et al. |
| 4,994,067 A | 2/1991 | Summers |
| 5,040,548 A | 8/1991 | Yock |
| 5,061,273 A | 10/1991 | Yock |
| 5,171,233 A | 12/1992 | Amplatz et al. |
| 5,350,395 A | 9/1994 | Yock |
| 5,358,479 A | 10/1994 | Wilson |
| 5,383,260 A | 1/1995 | Deschenes et al. |
| 5,431,673 A | 7/1995 | Summers et al. |
| 5,441,483 A | 8/1995 | Avitall |
| 5,451,233 A | 9/1995 | Yock |
| 5,487,757 A | 1/1996 | Truckai et al. |
| 5,495,974 A | 3/1996 | Deschenes et al. |
| 5,518,162 A | 5/1996 | Deschenes et al. |
| 5,569,277 A | 10/1996 | Evans et al. |
| 5,609,598 A | 3/1997 | Laufer et al. |
| 5,632,754 A | 5/1997 | Farley et al. |
| 5,728,129 A | 3/1998 | Summers |
| 5,810,882 A | 9/1998 | Bolduc et al. |
| 5,824,008 A | 10/1998 | Bolduc et al. |
| 5,865,800 A | 2/1999 | Mirarchi et al. |
| 5,868,767 A | 2/1999 | Farley et al. |
| 5,961,440 A | 10/1999 | Schweich, Jr. et al. |
| 5,964,772 A | 10/1999 | Bolduc et al. |
| 6,001,095 A | 12/1999 | de la Rama et al. |
| 6,001,127 A | 12/1999 | Schoon et al. |
| 6,036,715 A | 3/2000 | Yock |

(Continued)

FOREIGN PATENT DOCUMENTS

| | | |
|---|---|---|
| WO | WO 98/29041 A1 | 7/1998 |
| WO | WO 99/00059 | 1/1999 |
| WO | WO 99/13777 | 3/1999 |
| WO | WO 99/30647 A1 | 6/1999 |
| WO | WO 99/44534 A1 | 9/1999 |
| WO | WO 00/03759 | 1/2000 |
| WO | WO 00/06026 A2 | 2/2000 |
| WO | WO 00/06028 A1 | 2/2000 |
| WO | WO 00/66027 A2 | 2/2000 |
| WO | WO 00/16700 A1 | 3/2000 |

(Continued)

OTHER PUBLICATIONS

Messas, et al., "Chordal Cutting a New Therapeutic Approach for Ischmic Mitral Regurgitaion," 2001, American Heart Association Inc., pp. 1958–1963.

PCT Invitation to Pay Additional fees for PCT International Appln. No. US03/36633, mailed May 19, 2004 (5 pages).

Bonow, R., et al., "Guidelines for the Management of Patients With Valvular Heart Disease," Executive Summary, A Report of the American College of Cardiology/American Heart Association Task Force on Practice Guidelines (Committee on Management of Patients With Valvular Heart Disease), ACC/AHA Practice Guidelines, pp. 1949–1984.

*Primary Examiner*—David H. Willse
*Assistant Examiner*—Suzette J-J. Gherbi
(74) *Attorney, Agent, or Firm*—Blakely, Sokoloff, Taylor & Zafman LLP

(57) ABSTRACT

A medical device and method for treating a heart valve. In one embodiment, the medical device has a catheter, at least one needle disposed within the catheter, and a nonadjustable fastener ejectable from the needle.

55 Claims, 19 Drawing Sheets

U.S. PATENT DOCUMENTS

| | | |
|---|---|---|
| 6,045,497 A | 4/2000 | Schweich, Jr. et al. |
| 6,050,936 A | 4/2000 | Schweich, Jr. et al. |
| 6,059,715 A | 5/2000 | Schweich, Jr. et al. |
| 6,077,214 A | 6/2000 | Mortier et al. |
| 6,110,100 A | 8/2000 | Talpade |
| 6,123,699 A | 9/2000 | Webster, Jr. |
| 6,162,168 A | 12/2000 | Schweich, Jr. et al. |
| 6,165,119 A | 12/2000 | Schweich, Jr. et al. |
| 6,165,120 A | 12/2000 | Schweich, Jr. et al. |
| 6,165,164 A | 12/2000 | Hill et al. |
| 6,165,183 A | 12/2000 | Kuehn et al. |
| 6,165,197 A | 12/2000 | Yock |
| 6,178,346 B1 | 1/2001 | Amundson et al. |
| 6,182,664 B1 | 2/2001 | Cosgrove |
| 6,183,411 B1 | 2/2001 | Mortier et al. |
| 6,187,040 B1 | 2/2001 | Wright |
| 6,210,407 B1 | 4/2001 | Webster, Jr. |
| 6,210,432 B1 | 4/2001 | Solem et al. |
| 6,231,587 B1 | 5/2001 | Makower |
| 6,254,568 B1 | 7/2001 | Ponzi |
| 6,260,552 B1 | 7/2001 | Mortier et al. |
| 6,261,222 B1 | 7/2001 | Schweich, Jr. et al. |
| 6,264,602 B1 | 7/2001 | Mortier et al. |
| 6,269,819 B1 | 8/2001 | Oz et al. |
| 6,270,526 B1 | 8/2001 | Cox |
| 6,299,622 B1 | 10/2001 | Snow et al. |
| 6,312,447 B1 | 11/2001 | Grimes |
| 6,325,823 B1 | 12/2001 | Horzewski et al. |
| 6,355,030 B1 | 3/2002 | Aldrich et al. |
| 6,374,476 B1 | 4/2002 | Ponzi et al. |
| 6,402,780 B2 | 6/2002 | Williamson, IV et al. |
| 6,402,781 B1 | 6/2002 | Langberg et al. |
| 6,419,696 B1 | 7/2002 | Ortiz et al. |
| 6,461,366 B1 | 10/2002 | Seguin |
| 6,482,224 B1 | 11/2002 | Michler et al. |
| 6,493,575 B1 | 12/2002 | Kesten et al. |
| 6,500,167 B1 | 12/2002 | Webster, Jr. |
| 6,551,271 B2 | 4/2003 | Nguyen |
| 6,554,794 B1 | 4/2003 | Mueller et al. |
| 6,585,718 B2 | 7/2003 | Hayzelden et al. |
| 6,605,086 B2 | 8/2003 | Hayzelden et al. |
| 6,610,058 B2 | 8/2003 | Flores |
| 6,619,291 B2 | 9/2003 | Hlavka et al. |
| 6,626,899 B2 | 9/2003 | Houser et al. |
| 6,626,930 B1 | 9/2003 | Allen et al. |
| 6,629,534 B1 | 10/2003 | St. Goar et al. |
| 6,709,442 B2 * | 3/2004 | Miller et al. ................ 606/153 |
| 6,712,804 B2 * | 3/2004 | Roue et al. ................ 604/500 |
| 6,718,985 B2 | 4/2004 | Hlavka et al. |
| 6,719,767 B1 | 4/2004 | Kimblad |
| 6,810,882 B2 | 11/2004 | Langberg |
| 2001/0003986 A1 | 6/2001 | Cosgrove |
| 2001/0005787 A1 | 6/2001 | Oz et al. |
| 2001/0018611 A1 | 8/2001 | Solem et al. |
| 2001/0044568 A1 | 11/2001 | Langberg et al. |
| 2002/0010483 A1 | 1/2002 | Folmer et al. |
| 2002/0010486 A1 | 1/2002 | Hirt |
| 2002/0013571 A1 * | 1/2002 | Goldfarb et al. ................ 606/1 |
| 2002/0016628 A1 | 2/2002 | Langberg et al. |
| 2002/0026216 A1 | 2/2002 | Grimes |
| 2002/0035361 A1 | 3/2002 | Houser et al. |
| 2002/0042651 A1 | 4/2002 | Liddicoat et al. |
| 2002/0077647 A1 | 6/2002 | Snow et al. |
| 2002/0087173 A1 | 7/2002 | Alferness et al. |
| 2002/0103532 A1 | 8/2002 | Langberg et al. |
| 2002/0103533 A1 | 8/2002 | Langberg et al. |
| 2002/0161330 A1 | 10/2002 | Nguyen |
| 2002/0165484 A1 | 11/2002 | Bowe et al. |
| 2002/0165533 A1 | 11/2002 | Flores |
| 2002/0165534 A1 | 11/2002 | Hayzelden et al. |
| 2002/0188170 A1 * | 12/2002 | Santamore et al. ........... 600/37 |
| 2003/0050598 A1 | 3/2003 | Hayzelden et al. |
| 2003/0069593 A1 | 4/2003 | Tremulis et al. |
| 2003/0093071 A1 | 5/2003 | Hauck et al. |
| 2003/0120340 A1 | 6/2003 | Liska et al. |
| 2003/0120341 A1 | 6/2003 | Shennib et al. |
| 2003/0144732 A1 * | 7/2003 | Cosgrove et al. .......... 623/2.11 |
| 2003/0167071 A1 | 9/2003 | Martin et al. |
| 2003/0171776 A1 | 9/2003 | Adams et al. |
| 2003/0216764 A1 * | 11/2003 | Tu et al. ................... 606/167 |
| 2004/0010231 A1 * | 1/2004 | Leonhardt et al. ..... 604/170.03 |
| 2004/0044350 A1 | 3/2004 | Martin et al. |
| 2004/0044365 A1 * | 3/2004 | Bachman .................... 606/213 |
| 2004/0049207 A1 | 3/2004 | Goldfarb et al. |
| 2004/0059351 A1 * | 3/2004 | Eigler et al. ................ 606/148 |

FOREIGN PATENT DOCUMENTS

| | | |
|---|---|---|
| WO | WO 00/60995 | 10/2000 |
| WO | WO 01/00111 A1 | 1/2001 |
| WO | WO 01/00114 A1 | 1/2001 |
| WO | WO 01/26557 A1 | 4/2001 |
| WO | WO 01/28432 A1 | 4/2001 |
| WO | WO 01/28455 A1 | 4/2001 |
| WO | WO 01/49213 A2 | 7/2001 |
| WO | WO 01/49213 A3 | 7/2001 |
| WO | WO 01/54618 A1 | 8/2001 |
| WO | WO 01/89440 A2 | 11/2001 |
| WO | WO 02/00099 A2 | 1/2002 |
| WO | WO 02/01999 A2 | 1/2002 |
| WO | WO 02/34167 A2 | 5/2002 |
| WO | WO 02/39925 A2 | 5/2002 |
| WO | WO 02/053206 A2 | 7/2002 |
| WO | WO 02/062263 A2 | 8/2002 |
| WO | WO 02/062270 A1 | 8/2002 |
| WO | WO 02/062408 A2 | 8/2002 |
| WO | WO 03/049619 A2 | 6/2003 |
| WO | WO 03/073913 A2 | 9/2003 |
| WO | WO 04/012789 A2 | 2/2004 |
| WO | WO 04/014282 A2 | 2/2004 |

* cited by examiner

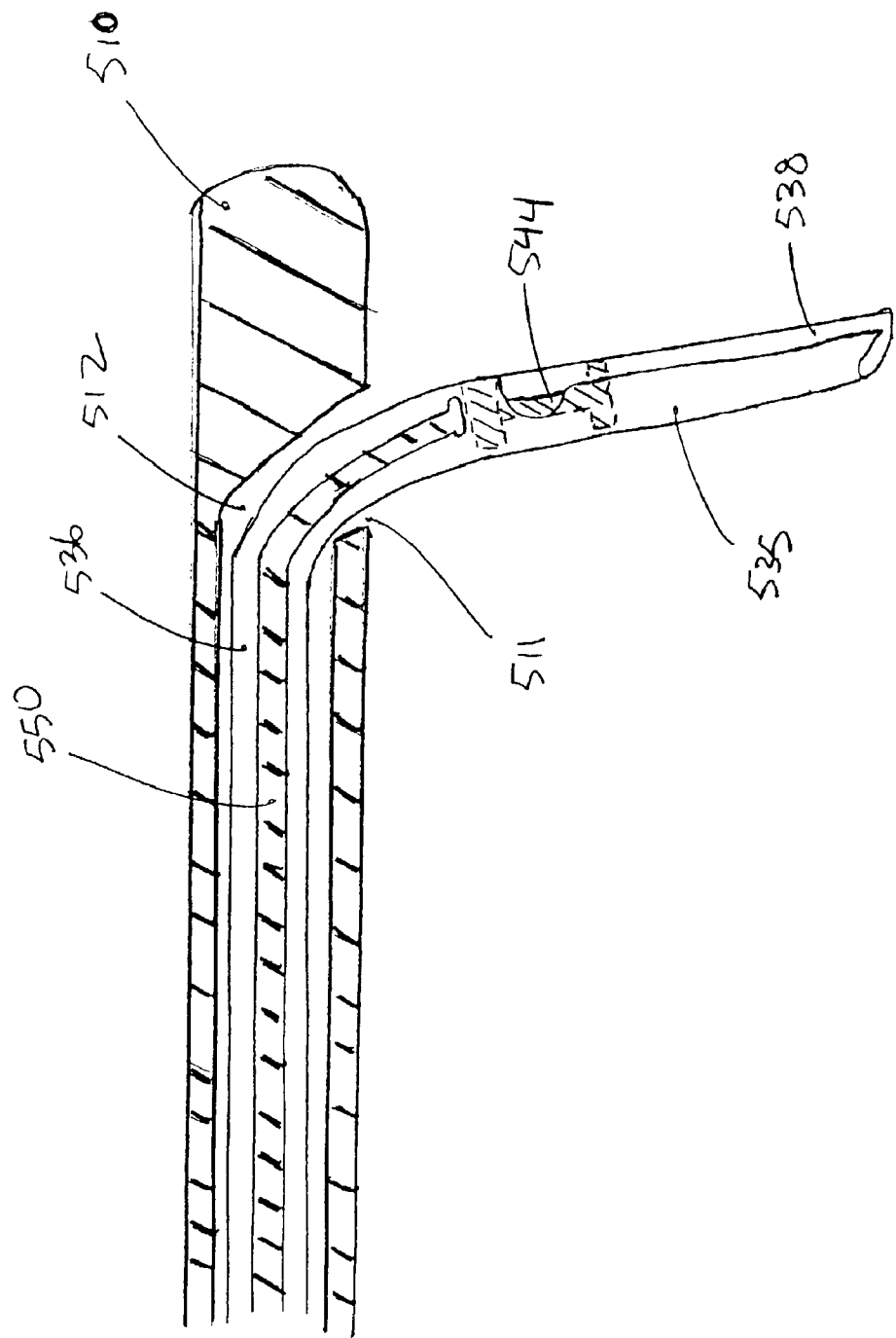

HEART VALVE CATHETER

TECHNICAL FIELD

The disclosure, in one embodiment, relates generally to the treatment of heart related diseases, and more particularly, in one embodiment, to the treatment of defective heart valves.

BACKGROUND

FIG. 1A illustrates a heart 10 with a partial internal view and arrows indicating the direction of blood flow within the heart. Four valves in the heart 10 direct the flow of blood within the left and right sides of the heart. The four valves include a mitral valve 20, an aortic valve 18, a tricuspid valve 60, and a pulmonary valve 62 as illustrated in FIG. 1A. The mitral valve 20 is located between the left atrium 12 and the left ventricle 14. The aortic valve 18 is located between the left ventricle 14 and the aorta 16. These two valves direct oxygenated blood coming from the lungs, through the left side of the heart, into the aorta 16 for distribution to the body. The tricuspid valve 60 is located between the right atrium 22 and the right ventricle 24. The pulmonary valve 62 is located between the right ventricle 24 and the pulmonary artery 26. These two valves direct de-oxygenated blood coming from the body, through the right side of the heart, into the pulmonary artery 26 for distribution to the lungs, where it again becomes re-oxygenated and distributed to the mitral valve 20 and the aortic valve 18.

The heart valves are complex structures. Each valve has "leaflets" that open and close to regulate the direction of blood flow. The mitral valve 20 has two leaflets and the tricuspid valve 60 has three leaflets. The aortic 18 and pulmonary 62 valves have leaflets that are referred to as "cusps," because of their half-moon like shapes. The aortic 18 and pulmonary 62 valves each have three cusps.

During diastole, the leaflets of the mitral valve 20 open, allowing blood to flow from the left atrium 12 to fill the left ventricle 14. During systole, the left ventricle 14 contracts, the mitral valve 20 closes (i.e., the leaflets of the mitral valve 20 re-approximate), and the aortic valve 18 opens allowing oxygenated blood to be pumped from the left ventricle 14 into the aorta 16. A properly functioning mitral valve 20 allows blood to flow into the left ventricle and prevents leakage or regurgitation of blood back into the left atrium (and subsequently back into the lungs). The aortic valve 18 allows blood to flow into the aorta 16 and prevents leakage (or regurgitation) of blood back into the left ventricle 14. The tricuspid valve 60 functions similarly to the mitral valve 20 to allow deoxygenated blood to flow into the right ventricle 24. The pulmonary valve 62 functions in the same manner as the aortic valve 18 in response to relaxation and contraction of the right ventricle 24 (i.e., to move de-oxygenated blood into the pulmonary artery 26 and subsequently to the lungs for re-oxygenation).

During relaxation and expansion of the ventricles 14, 24, (i.e., diastole), the mitral 20 and tricuspid 60 valves open, while the aortic 18 and pulmonary 62 valves close. When the ventricles 14, 24, contract (i.e., systole), the mitral 20 and tricuspid 60 valves close and the aortic 18 and pulmonary 62 valves open. In this manner, blood is propelled through both sides of the heart (as indicated by the arrows of FIG. 1A).

Regurgitation is a condition in which leaflets of a heart valve do not close completely, resulting in the backflow of blood. For instance, in a condition typically referred to as mitral valve prolapse (also known as mitral valve regurgitation), the leaflets of the mitral valve do not close completely during systole and blood leaks back into the left atrium. The heart is then forced to work harder to pump enough oxygenated blood to the body. This may lead to heart damage over a period of time. Regurgitation is common, occurring in approximately 7% of the population. Mitral valve regurgitation may be caused by a number of conditions, including genetic defects, infections, coronary artery disease (CAD), myocardial infarction (MI), or congestive heart failure (CHF).

Faulty or defective valves may be treated with various surgical procedures. Annuloplasty, illustrated in FIG. 1B, is one type of a surgical procedure that has been used to treat regurgitation. Annuloplasty 30 involves a synthetic ring 32 that is placed around a valve rim (annulus) 34 of a heart valve. Sutures 38 attach the valve annulus 34 to the synthetic ring 32. Synthetic ring 32 reduces the size of valve opening 36, causing the valve to close properly. FIG. 1C illustrates another surgical procedure in which a heart valve such as the mitral valve 20 is repaired by reconstruction. First, at step A, a section P2 from the posterior leaflet 40 of the mitral valve 20 is excised. Then, sequentially at steps B, C, D, and E, sections P1 and P3 of the posterior leaflet 40 are sutured together. The reconstruction shrinks the size of the valve opening 36. In some instances, a faulty or defective valve must be surgically replaced with a new valve. Examples of new valves include homograft valves (valves harvested from human cadavers), artificial mitral valves, and mechanical valves.

The procedures discussed above are typically major, invasive surgical procedures that may require opening the chest by sternotomy, making incisions in the chest wall, heart-lung bypass and suspending the beating of the heart. These invasive procedures subject patients to a tremendous amount of pain and discomfort. Moreover, these procedures require lengthy recovery and/or hospitalization periods. Patients with congestive heart failure may not be able to tolerate the surgical procedures described above, leaving them with little or no alternative to treat their defective heart valves. An example of a percutaneous system for mitral valve repair is described in U.S. Patent Application Publication No. US 2002/0013571A1.

SUMMARY

Embodiments of a medical device and methods for percutaneously treating a heart valve are described. In one embodiment, the medical device has a catheter, at least one needle disposed within the catheter, and a nonadjustable fastener ejectable from the needle.

Additional embodiments, features, and advantages of the medical device will be apparent from the accompanying drawings, and from the detailed description that follows below.

BRIEF DESCRIPTION OF THE DRAWINGS

The present disclosure is illustrated by way of example, and not limitation, in the figures of the accompanying drawings in which:

FIG. 5A illustrates a side view of the needle extending from a distal portion shown in FIG. 5.

DETAILED DESCRIPTION

Figure 1A:
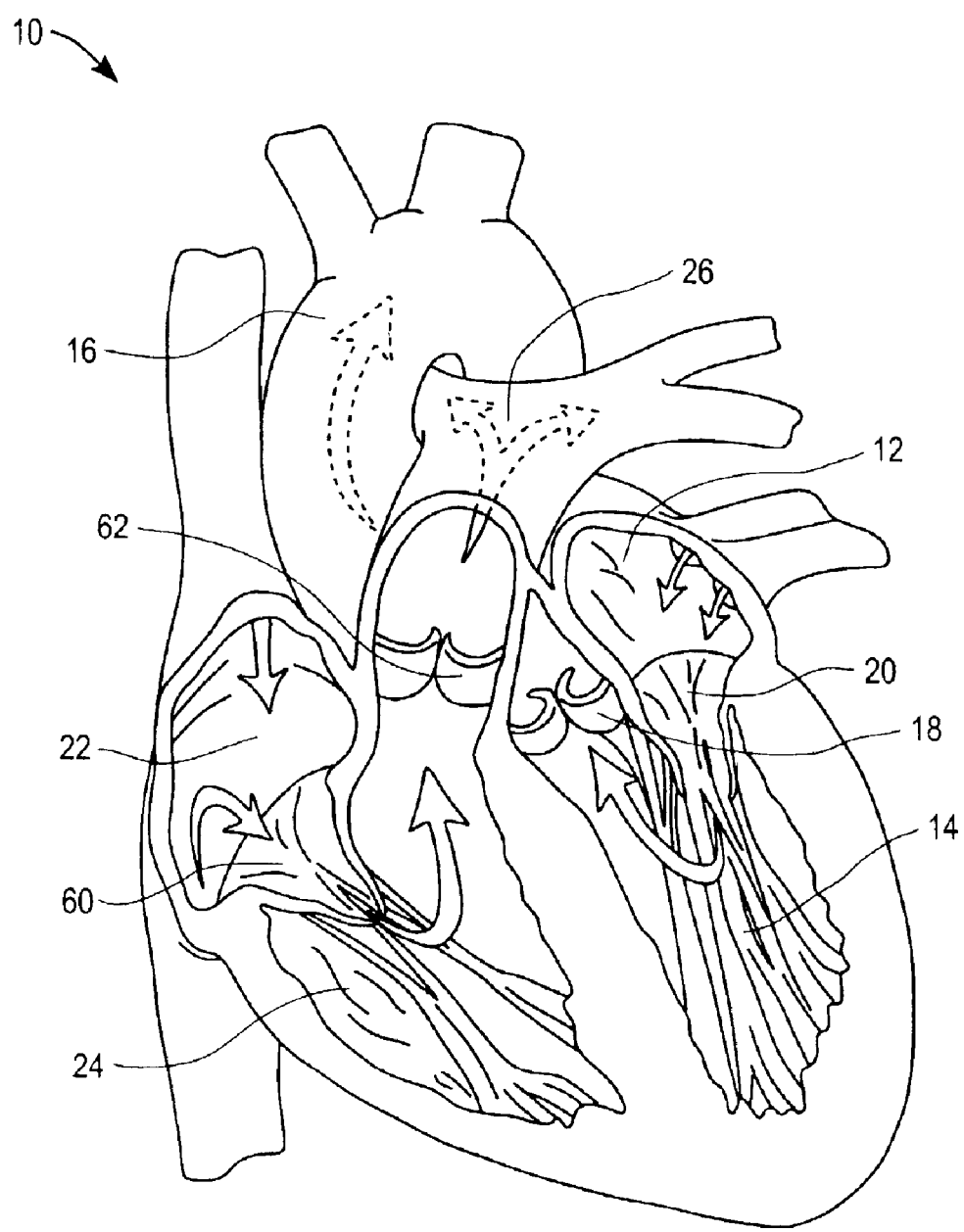
FIG. 1A illustrates a heart.
Figure 1B:
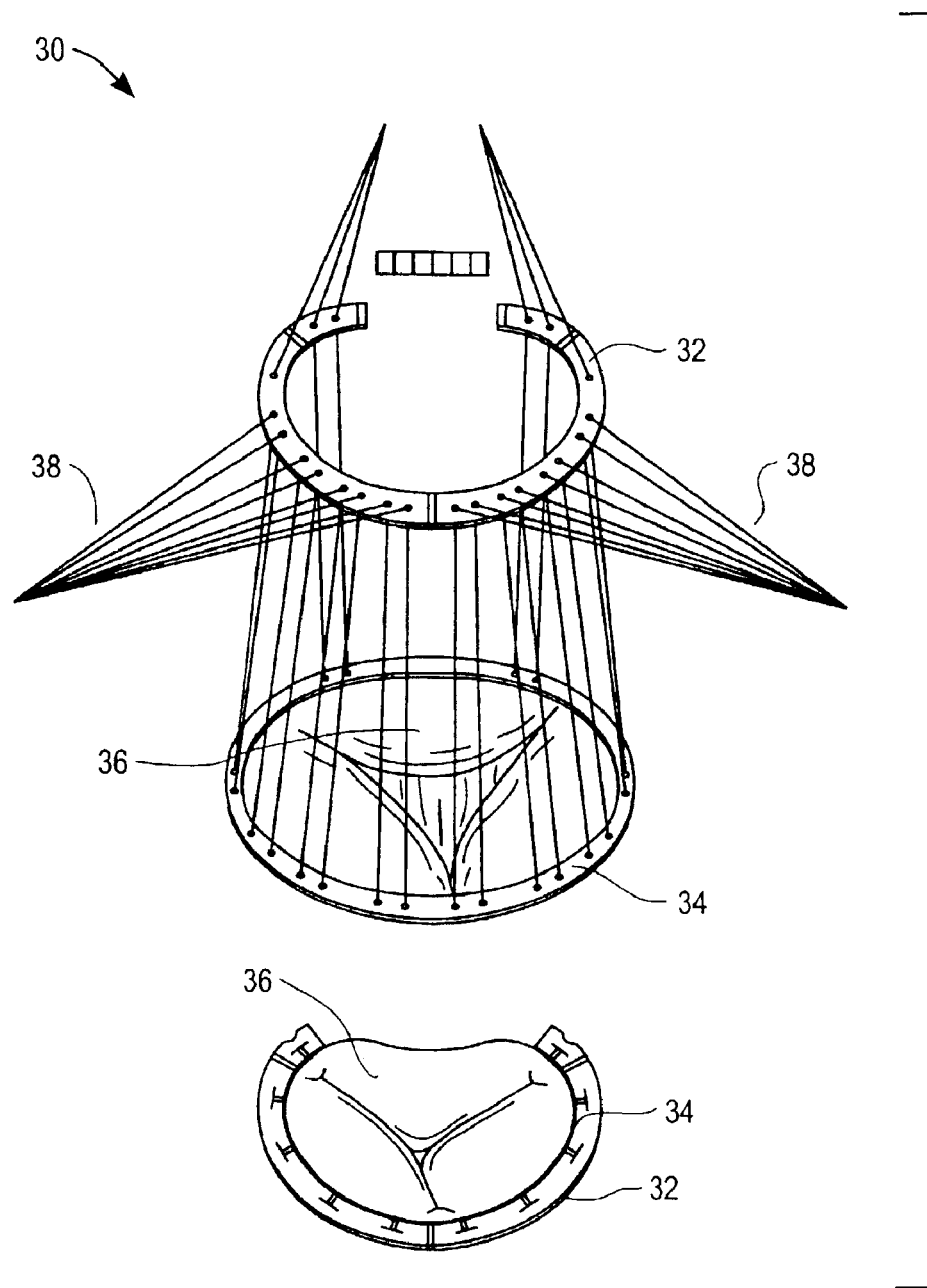
FIG. 1B illustrates an annuloplasty procedure to constrict a defective valve.
Figure 1C:
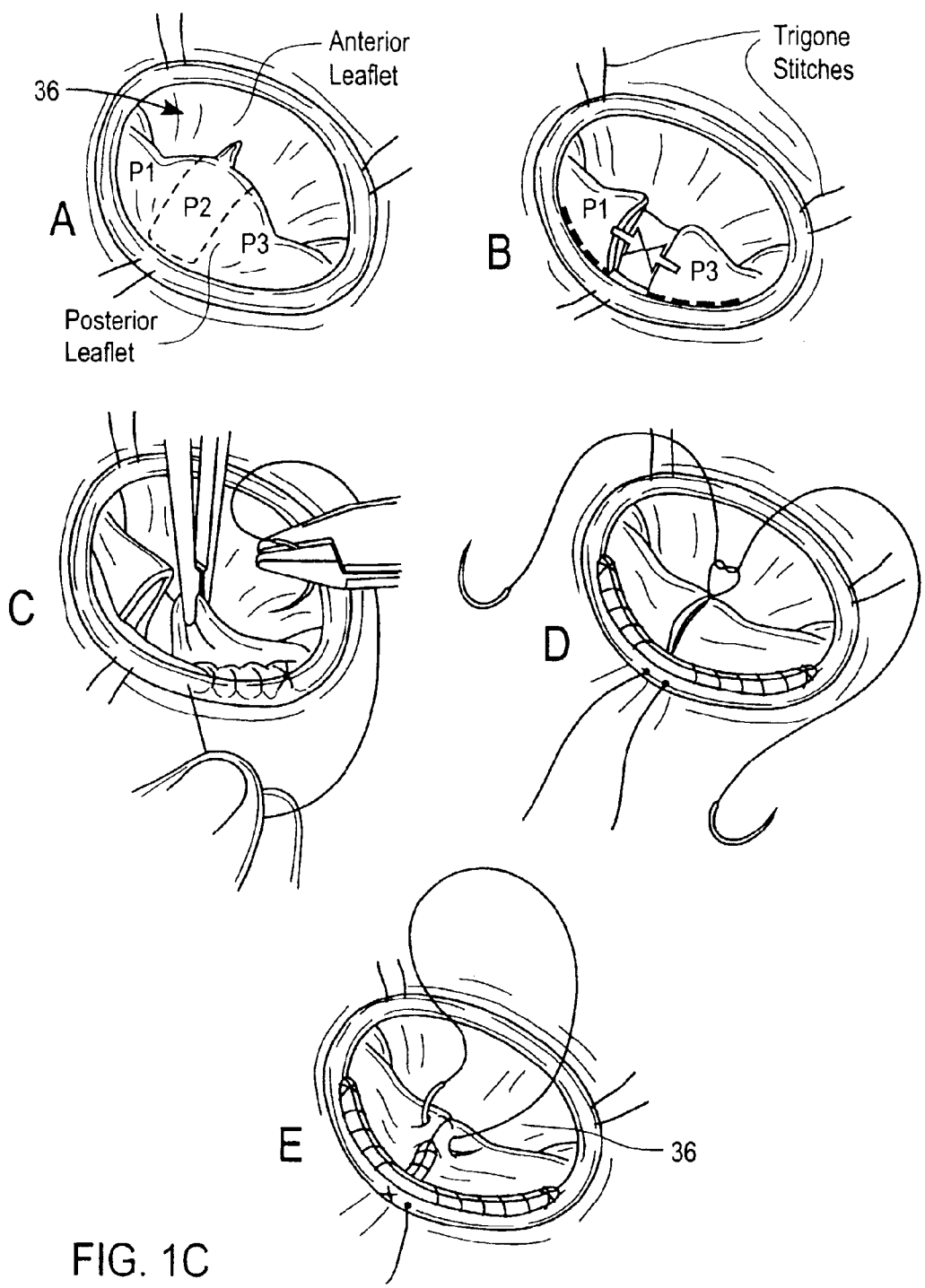
FIG. 1C illustrates a reconstruction procedure to reduce the size of a defective valve.

In the following description, numerous specific details are set forth such as examples of specific materials or components in order to provide a thorough understanding of the present disclosure. It will be apparent, however, to one skilled in the art that these specific details need not be employed to practice the disclosure. In other instances, well known components or methods have not been described in detail in order to avoid unnecessarily obscuring the present disclosure. Embodiments of a medical device discussed below are described with respect to the treatment of a mitral valve. It may be appreciated, however, that other heart valves or body tissue may be treated, and embodiments of the medical device are not limited in their applicability to treating the mitral valve.

Embodiments of a medical device and methods for treating the mitral valve percutaneously are described. A medical device, in one embodiment, may be used to treat mitral valve regurgitation or prolapse. In one embodiment, the medical device includes an elongated catheter having a proximal portion and a distal portion. At least one stabilizer is extendable from a distal portion of the catheter to grasp and restrict the movement of a mitral valve leaflet. In an alternative embodiment, the medical device may have two stabilizers, one for each leaflet. At least one needle, disposed within a housing extendable from the catheter, has a fastener that may be ejected from the needle. The fastener, in one embodiment, has a fixed, nonadjustable elongated central portion with disk-shaped ends. Alternatively, the fastener may have cylindrical-shaped ends perpendicular to the elongated central portion.

In one method for treating a mitral valve, after inserting percutaneously a catheter through a patient's vasculature so that a distal end of the catheter is near the mitral valve, a first stabilizer is extended from a distal portion of a catheter to grasp and restrict the movement of a first mitral valve leaflet. A second stabilizer is extended from the catheter to grasp and restrict the movement of a second mitral valve leaflet. A needle, initially retracted within the distal portion of the catheter, extends to penetrate through the first and second mitral valve leaflets. A fastener is then ejected from the needle such that the elongated central portion of the fastener passes through both leaflets. The disk-shaped ends of the fastener holds the two leaflets together. This medical device, in one embodiment, provides the advantages of deploying a mitral valve fastener without the need for additional actions to secure the fastener to the mitral valve leaflets (e.g., suturing the ends of the fastener together). Once the needle has penetrated through the leaflets, the fastener may be ejected, and the catheter removed. Moreover, because the fastener is deployed percutaneously, the method requires only a minimally invasive procedure, in contrast to surgical procedures which require opening the chest cavity to access the mitral valve.

Figure 2:
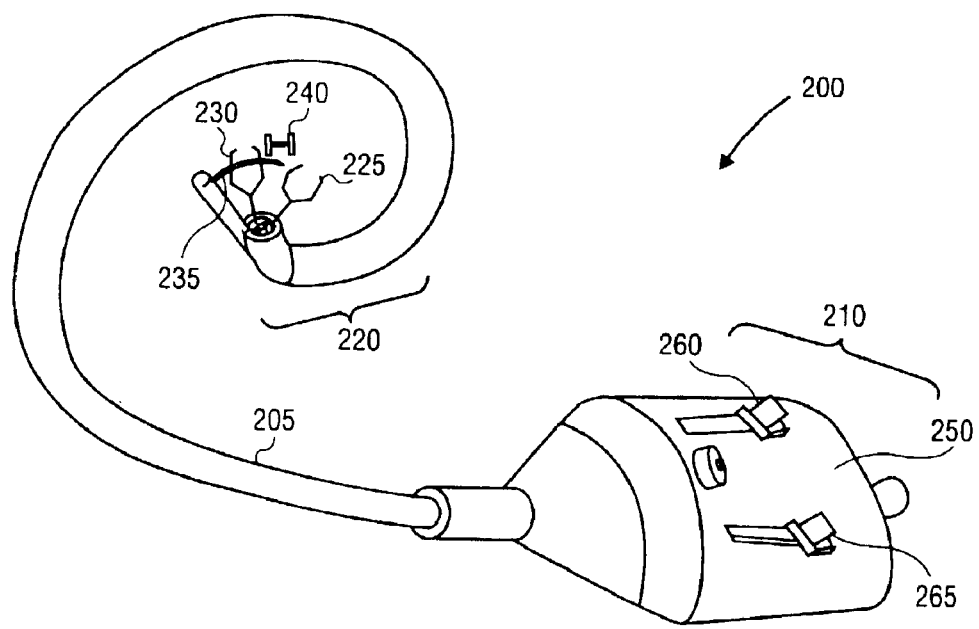
FIG. 2 illustrates one embodiment of a percutaneous medical device to treat a mitral valve.

Referring now to FIG. 2, one embodiment of a medical device to treat a mitral valve is illustrated. Medical device 200 is adapted and sized for percutaneous advancement within a body lumen (e.g., to be advanced to the mitral valve region of the heart). The medical device 200 has a proximal portion 210 and a distal portion 220. An elongated catheter 205 couples proximal portion 210 to distal portion 220. Distal portion 220 includes a first stabilizer 225 and a second stabilizer 230 that may extend from distal portion 220 of medical device 200. First and second stabilizers 225, 230 may completely retract within catheter 205 in one position. In an extended position, in one embodiment, first and second stabilizers 225, 230, are C-shaped to rivet a leaflet of a mitral valve or other body tissue. A needle 235, also having a retracted and extended position, may be disposed within a distal portion 220 of medical device 200. In one embodiment, needle 235, may be adapted to penetrate or pierce through one or both leaflets of the mitral valve. Needle 235, disposed near first and second stabilizers 225, 230, may penetrate the leaflets being held by first and second stabilizers 225, 230. A fastener 240 is illustrated in an ejected position from needle 235. As described in greater detail below, fastener 240 is designed and structured to hold one or both mitral valve leaflets as they are between its two ends. As such, medical device 200 may eject and secure mitral valve leaflets in a single action; no additional procedures are required to secure the leaflets with fastener 240 (e.g. adjusting a length and/or securing fastener 240).

Proximal portion 210 of medical device includes a control mechanism 250 to regulate the various parts of the distal portion 220 (e.g., first and second stabilizers 225, 230, and needle 235). Control mechanism 250 may also include controls to steer distal portion 220 (e.g., pull tendons within catheter 205), because distal portion 220 may require accurate positioning around the mitral valve for delivering fastener 240. First and second control elements 260, 265 may control various aspects of distal portion 220 for example, extending and/or retracting first and second stabilizers 225, 230, extending and/or retracting needle 235, and ejecting fastener 240. In an alternative embodiment, control mechanism 250 may have more control elements in addition to first and second control elements 260, 265 shown in FIG. 2.

Figure 3:
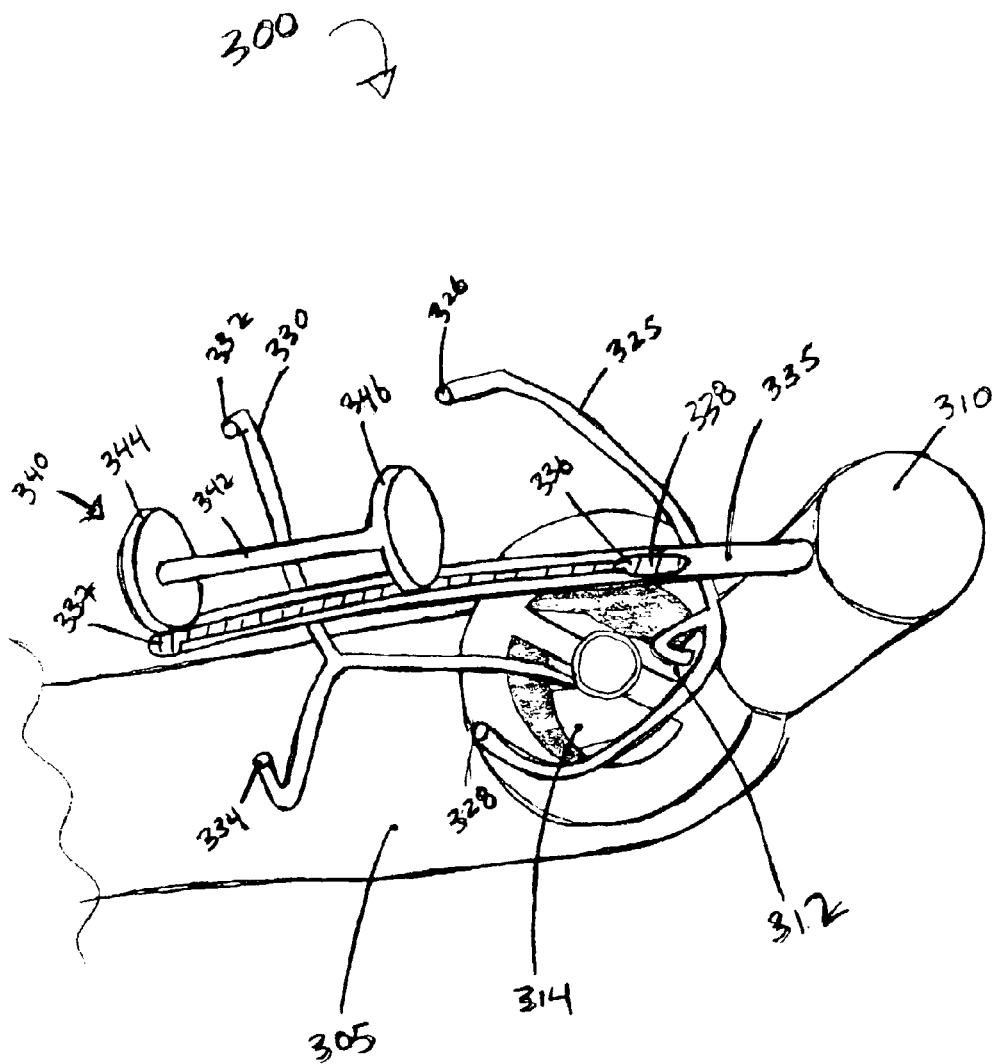
FIG. 3 illustrates one embodiment of a distal portion of a percutaneous medical device to treat a mitral valve.

FIG. 3 illustrates one embodiment of a distal portion 300 of a medical device (e.g., medical device 200 of FIG. 2) to treat a mitral valve. As illustrated, catheter 305 has been steered such that distal portion 300 has been angled relative to catheter 305. Distal portion 300 illustrates various elements in a fully extended and/or ejected position. A first stabilizer 325 extends out from a first opening 312, and a second stabilizer 330 extends out from a second opening 314 of catheter 305. In one embodiment, first and second stabilizers 325, 330, may be C-shaped to locate and grasp a mitral valve leaflet. In one embodiment, first and second stabilizers 325, 330 may be made of flexible material (e.g., polymers, plastics, metals, shape-memory alloys such as nickel titanium). Alternatively, first and second stabilizers 325, 330 may be made out of metals, plastic, or any other hard materials that are biocompatible or suitable for use in a patient's body. Stabilizers 325, 330 may also be made out of polymers, high-density polyethylene (HDPE), polyglycolic acid, and polyglycolic hydroxyacetic acid.

The flexible properties of first and second stabilizers 325, 330 enable the distal ends (326, 328, 332, 334) to open and close towards each other. For example, when first stabilizer 325 is retracted within first opening 312, ends 326, 328 are flexed towards one another thereby minimizing its size to fit within first opening 312. When first stabilizer 325 extends out, ends 326, 328 expand from each other, as illustrated, to a size larger than first opening 312. By partially retracting first stabilizer 325, ends 326, 328 close toward each other. In use, first stabilizer 325 may be extended to locate a mitral valve leaflet and then retracted (e.g., pulled back into the opening 312) until ends 326, 328 close towards each other to rivet the leaflet. When positioned over a mitral valve leaflet, ends 326, 328 may stabilize the leaflet (not shown). Second stabilizer 330 with ends 332, 334 may perform similarly to first stabilizer 325 and its corresponding ends 326, 328. First and second stabilizers 325, 330 also enable a user to manipulate and control the movement of mitral valve leaflets. For example, first and second stabilizers 325, 330 may be used to restrict the leaflets and bring them closer together before ejecting fastener 340 between them. It may be appreciated by one skilled in the art that in one embodiment, the medical device may not require first and second stabilizers 325, 330 for the delivery of fastener 340. For example, the distal portion 300 may have one stabilizer only, or more than the two stabilizers.

Needle 335 extends from needle housing 310 in a direction substantially perpendicular to first and second stabilizers 325, 330. In a retracted position, needle 335 may be completely enclosed within housing 310 and transverse to the end of needle housing 310. In the extended position, needle 335 has a length sufficiently long enough to cover a distance between first stabilizer 325, and second stabilizer 330. Needle 335 also has slot 338 extending towards the needle tip. Needle slot 338 enables fastener 340 to be ejected from needle 335. Needle slot 335 may have a proximal opening 336 and a distal opening 337 allowing for more than one opening to release fastener 340. Needle 335, in one embodiment, is sufficiently rigid to penetrate through body tissue. For example, needle 335 may be made of stainless steel or ceramics. Needle 335 may also have flexible properties.

Fastener 340 is illustrated fully released from needle 335. In one embodiment, fastener 340 has an elongated central portion 342 with disk-shaped ends 344, 346. In an alternative embodiment, fastener 340 may have elongated central portion 342 with cylindrical-shaped ends parallel to each other and perpendicular to elongated central portion 342 (not shown). Fastener 340 is designed and structured to maintain the mitral valve leaflets between ends 344, 346. Because fastener 340 is released after needle 335 has penetrated through the leaflets, central portion 342 of fastener 340 passes through both leaflets as well. The deployment of fastener 340 is provided in greater detail below. The fastener 340 will normally be flexible, and at least ends 344 and 346 will be compressible to allow the ends 344 and 346 to fit within the lumen of the needle 335.

In one embodiment, fastener 340 has an elongated central portion 342 of a fixed length and is continuous with ends 344, 346 to form a unitary piece. As such, when ejected, fastener 340 does not require additional procedures or actions to connect ends 344, 346 to elongated central portion 342. The structure of fastener 340 provides an advantage over fasteners which may require suturing one end to the other. Although the length of elongated central portion 342 may not be adjustable in certain embodiments, a fastener having any desired length may be loaded into needle 335 for delivery to the mitral valve leaflets. In one embodiment, fastener 340 may have a length in range of approximately 0.1 mm to 20 mm.

Figure 12:
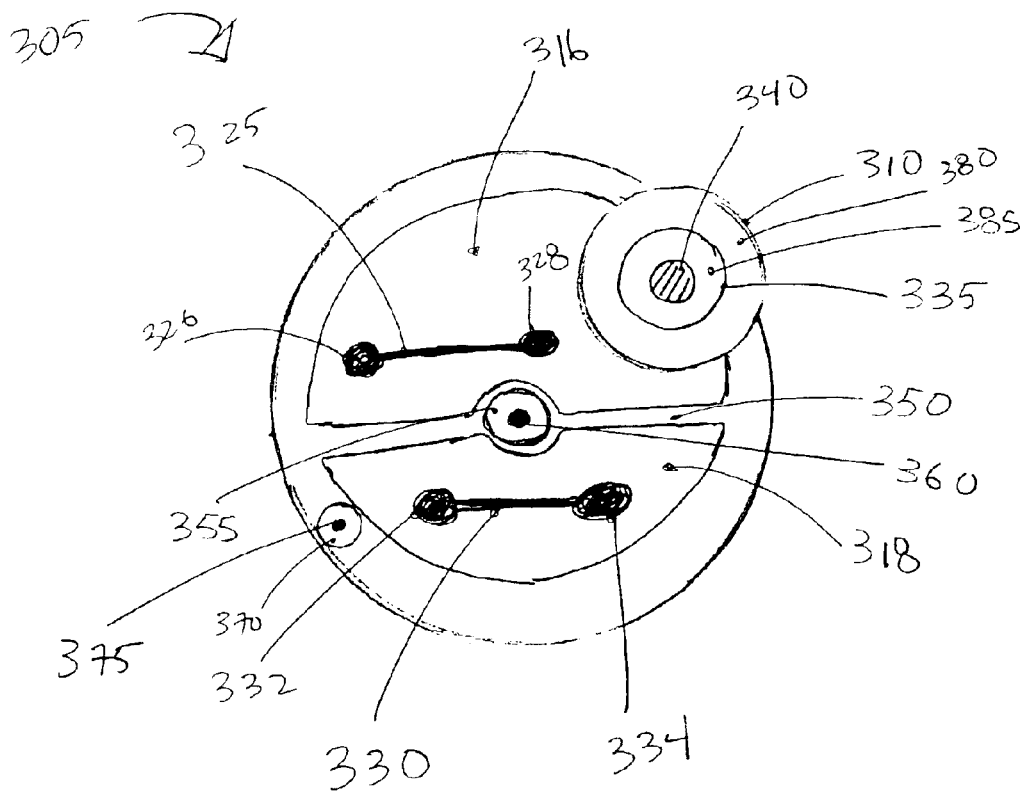
FIG. 12 illustrates a cross-sectional view of one embodiment of a distal portion of a percutaneous medical device to treat a mitral valve.

FIG. 12 illustrates a cross-sectional view of one embodiment of a distal portion of a percutaneous medical device to treat a mitral valve (e.g. portion 300 of catheter 305 of described above). Lumens 316, 318 are formed within catheter 305 by partition 350 disposed substantially across a central portion of catheter 305. Lumen 316 contains first stabilizer 325 and lumen 318 contains 330. First stabilizer 325 is illustrated, in one embodiment, with ends 326, 328 and second stabilizer 330 is illustrated with ends 332, 334. Partition 350 also forms a lumen 355 which may contain a guidewire 360. The first stabilizer 325, the second stabilizer 330 and the guidewire 360 extend from the controls at the proximal end to the distal end in certain embodiments, thereby allowing a user to control the extension and retraction of the stabilizers and to allow the catheter to be guided by the guidewire. Needle housing 310 is disposed near an edge of catheter 305. A needle lumen 380 may be formed within needle housing 310 that contains needle 335. Fastener 340 may be disposed within a needle lumen 385 formed within needle 335. Also within the lumen 385 is a push rod (not shown in the cross section of FIG. 12) which is proximally positioned relative to the fastener 340 so that the fastener 340 may be pushed out the distal end of the needle 335. This push rod extends from a control mechanism near the proximal end of the catheter 305 to a position abutting the fastener 340. Additionally, catheter 305 may also have lumen 370 in which a steering wire 375 (e.g., a pull tendon) may be disposed therein. Wire 375 enables distal portion 300 of catheter 305 to steer and position itself near the mitral valve leaflets once it has been advanced to the left ventricle. Wire 375 may be manipulated by a control mechanism (e.g., control mechanism 250 discussed above). The wire 375 extends, in certain embodiments, from the control mechanism to near the distal end.

Figure 4:
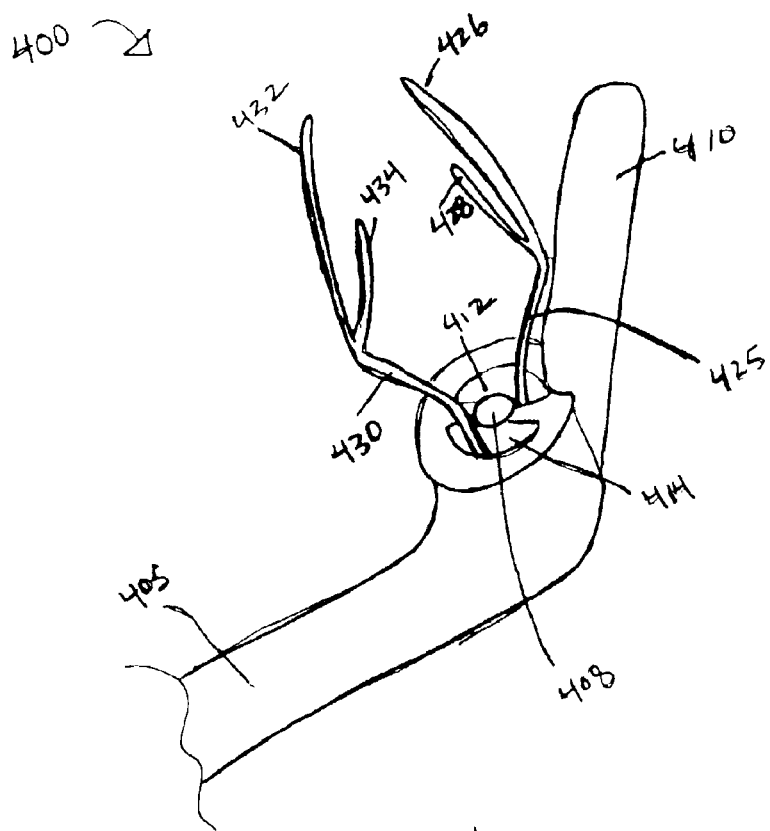
FIG. 4 illustrates one embodiment of stabilizers extending from a distal portion of a percutaneous medical device to treat a mitral valve.

FIG. 4 illustrates one embodiment a distal portion 400 of a medical device to treat a mitral valve and is similar to portion 300 shown in FIG. 3. Distal portion 400 includes elongated catheter 405 that is flexible or steerable as shown. A distal end of catheter 405 has first opening 412 and second opening 414. Catheter 405 may also have a guidewire lumen 408 formed between the lumens corresponding to first and second openings 412, 414. First stabilizer 425 with stabilizer ends 426, 428 extends from first opening 412 and second stabilizer 430 with stabilizer ends 432, 434 extends from second opening 414. Needle housing 410 extends from the distal end of catheter 405. As discussed above, housing 410 contains a needle (e.g., needle 335). However, as shown in FIG. 4, the needle has not been extended out of needle housing 410. FIG. 4 illustrates one embodiment a medical device in which first and second stabilizers may grasp and hold leaflets of the mitral valve. The steerability and control of first and second stabilizers 325, 330 enable them to manipulate the mitral valves mechanically.

Figure 5:
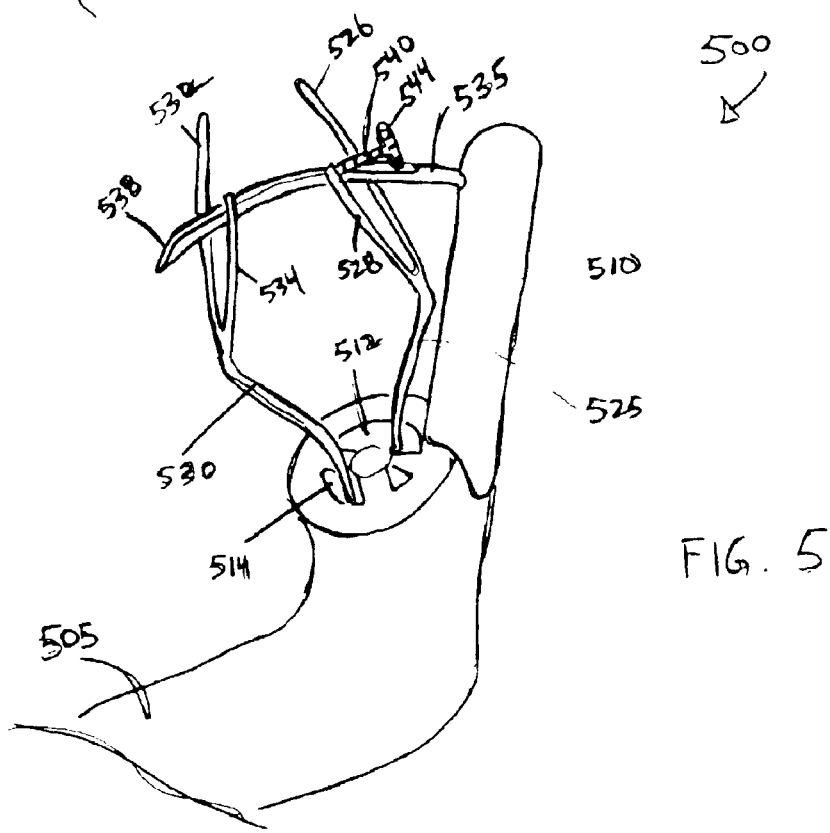
FIG. 5 illustrates one embodiment of a needle extending from a distal portion of a percutaneous medical device to treat a mitral valve.

FIG. 5 illustrates one embodiment of a fastener 540 prior to its complete ejection from needle 535. The portion 500 in FIG. 5 is similar to portion 400 FIG. 4 and portion 300 in FIG. 3, having a distal portion of catheter 505 with needle 535 extending from needle housing 510. First stabilizer 525 and second stabilizer 530 are in a fully extended position from first opening 512 and second opening 514, respectively. Needle 535 extends between ends 526, 528 of first stabilizer 525 and ends 532, 534 of second stabilizer 530. As discussed above, needle 535 has a slot 538 to enable fastener 540 to be released. Fastener end 544 is illustrated partially ejected from slot 538 near a proximal end of needle 535. An opposing end (not shown) of fastener 540 may be released near a distal tip of needle 540. Alternatively, fastener 540 may be ejected anywhere along slot 538.

FIG. 5A illustrates a side view of needle 535 extending from needle housing 510. Needle housing 510 forms a lumen 512 that ends in opening 511 to advance needle 535 out from needle housing 510. Needle 535 has a lumen 536 for advancing fastener 544 toward slot 538 formed near a distal portion of needle 535. A push rod or mandrel 550 may also be disposed within lumen 536 of needle 535 to eject fastener 544 from slot 538. As shown, needle 535 may be flexible enough to bend when extended from housing 510, but may also be rigid enough to penetrate through body tissue (e.g. mitral valve leaflets).

Figure 6:
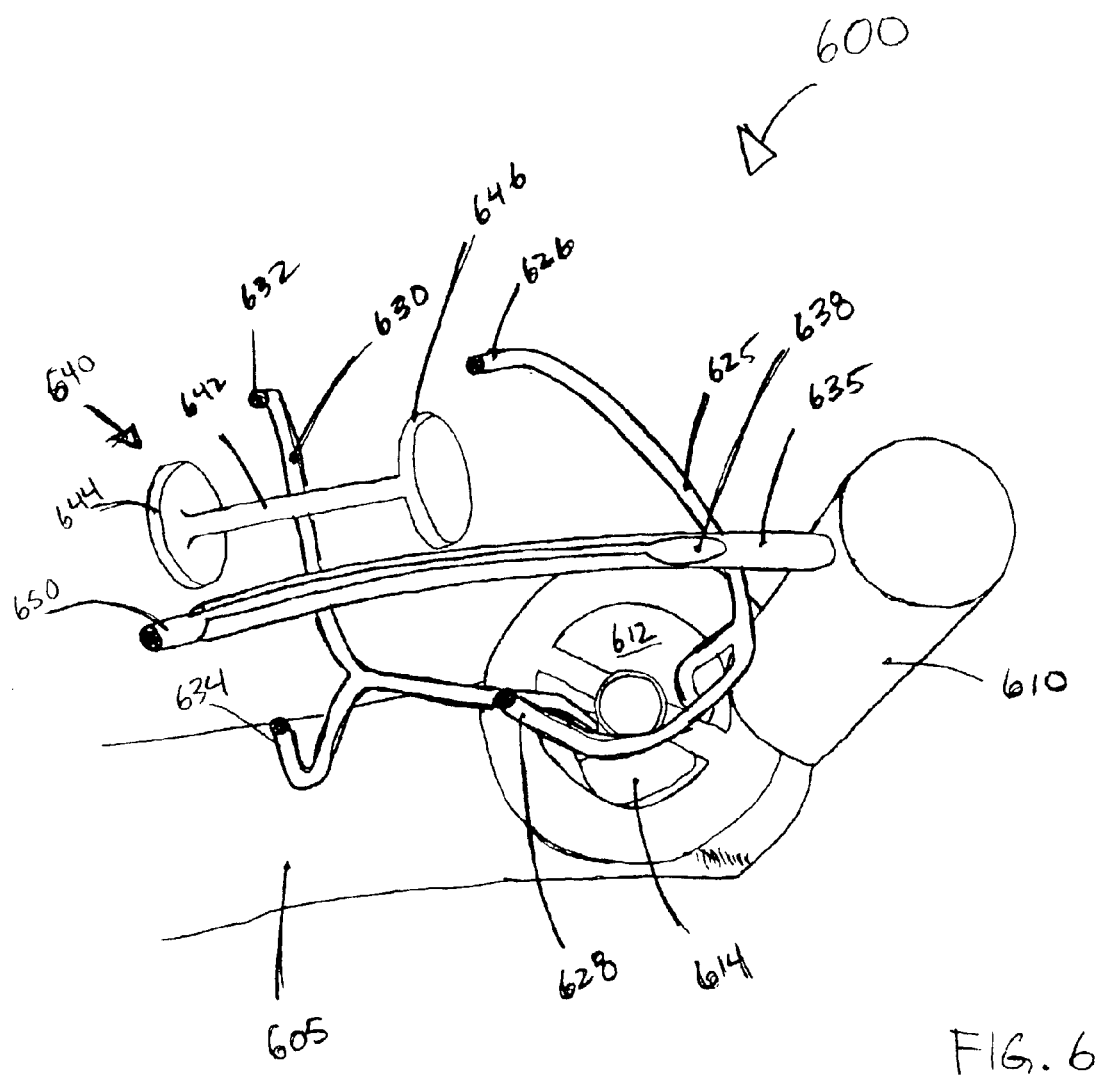
FIG. 6 illustrates another embodiment of a distal portion of a percutaneous medical device to treat a mitral valve.

FIG. 6 illustrates another embodiment of a fastener 640 ejected from needle slot 638 by a mandrel 650 also disposed within needle 635. Mandrel 650 may be, in one embodiment, an elongated push rod controlled with a mechanism (e.g., control mechanism 250 of FIG. 2) disposed near a proximal portion of catheter 605 and this pushrod extends within the lumen of the needle 635, from the control mechanism to the distal end of needle 635, in one embodiment as shown in FIG. 6. By advancing mandrel 650 towards a distal end of needle 635, fastener 640 is ejected from slot 638. As illustrated, fastener 640 has been fully ejected from needle 635. When released, fastener 640, having an elongated central portion 642, and disk-shaped ends 644, 646 may be positioned between first stabilizer 625 and second stabilizer 630. Needle 635 extends at an angle (e.g., substantially perpendicular) from housing 610 towards first and second stabilizers 625, 630. Upon release of fastener 640, first and second stabilizers 625, 630 may be retracted into first and second openings 612, 614, respectively, of catheter 605.

As discussed above, fastener 640 is not limited to a design of an elongated central portion with disk-shaped ends. In an alternative embodiment, the fastener may have ends that are short bars perpendicular to an elongated central portion, or a combination of one end having a disk-shape with an opposite end having a bar-shape. It may be appreciated by one of skill in the art that the fastener ends may have of a variety of shapes to hold mitral valve leaflets. Moreover, it may be appreciated by one of skill in the art that first and second stabilizers 625, 630 may have shapes and designs not limited to ends 626, 628 and 632, 634. Alternatively, the stabilizer ends may have sharp tips that penetrate through leaflets or ridges that mate with the opposing tip. It may be appreciated that the stabilizer ends may have any number of structures to grasp or hold leaflets and/or body tissue.

Figure 13:
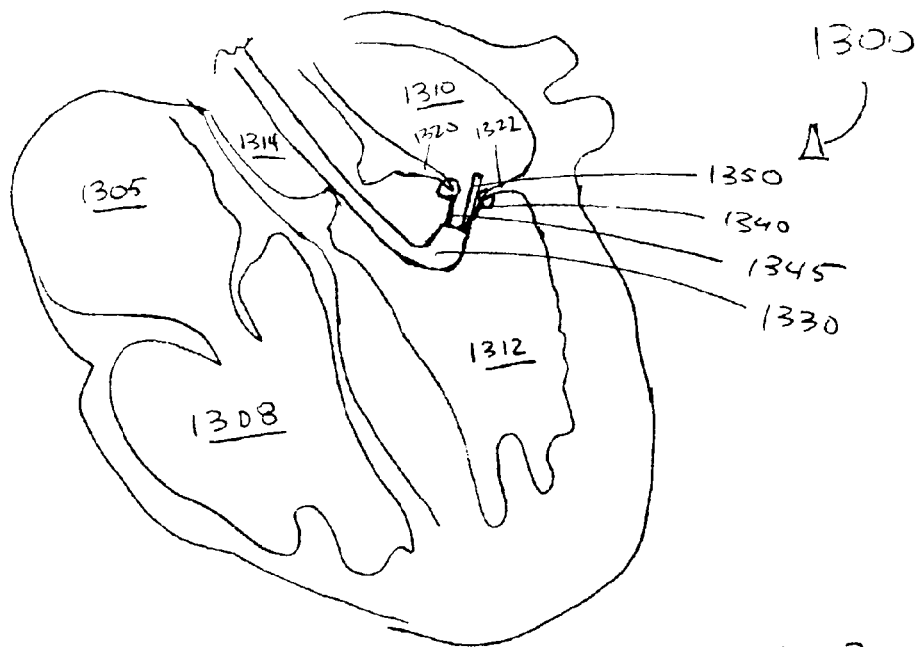
FIG. 13 illustrates a cross-sectional view of a heart with a catheter advanced to a mitral valve region.

FIGS. 13–16 and 18, described collectively, illustrate one exemplary method of deploying a mitral valve leaflet fastener with the embodiments of the medical device described above (e.g., with respect to the devices shown in FIGS. 2–6 and described relative to these FIGS. 2–6). FIG. 13 illustrates a simplified cross-sectional view of the heart with a distal portion 1330 of a catheter that has been percutaneously advanced to the mitral valve. The chambers of the heart are illustrated as right atrium 1305, right ventricle 1308, left atrium 1310, and left ventricle 1312. A guidewire (not shown) may be initially positioned across mitral valve leaflets 1320, 1322 by coming, through a retrograde approach, down aortic valve 1314 and up through left ventricle 1312. Catheter 1330 may be loaded and tracked over the guidewire to be positioned near leaflets 1320, 1322. In other embodiments, catheter 1330 may be any of the catheter types used in the art, including but not limited to "rapid exchange" (RX) catheters, "over-the-wire" (OTW) catheters, or a "tip RX" catheters. Catheter 1330 typically includes a portion of the catheter which is adapted to be disposed through the aortic valve. Various imaging techniques known in the art may also be used to locate the mitral valve leaflets. For example, echo imaging, infrared illumination, x-ray, and magnetic resonance imaging methods may be utilized. These imaging techniques are known in the art; accordingly, a detailed description is not provided. First stabilizer 1340 has been extended from catheter 1330 to hold leaflet 1322 and second stabilizer 1345 has been extended to hold leaflet 1320. As discussed above, stabilizers 1340, 1345 position the leaflets together so that a fastener may be ejected across them. The stabilizers may grasp the leaflets as the stabilizer is extended out of the catheter and the stabilizer can be tightened onto the leaflets by retracting the stabilizer while the leaflet is within the arms of the stabilizers. Because a fastener may be deployed while the heart is beating, leaflets 1320, 1322 may need to be mobilized. Needle housing 1350 is also illustrated extending from catheter 1330.

Figure 14:
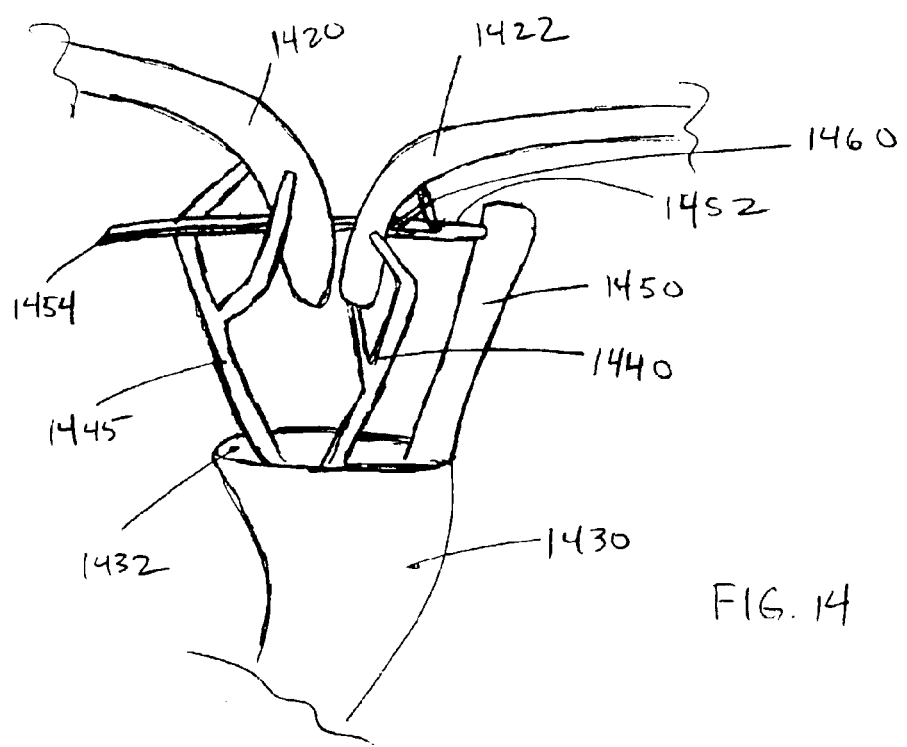
FIG. 14 illustrates one embodiment of ejecting a mitral valve leaflet fastener.
Figure 15:
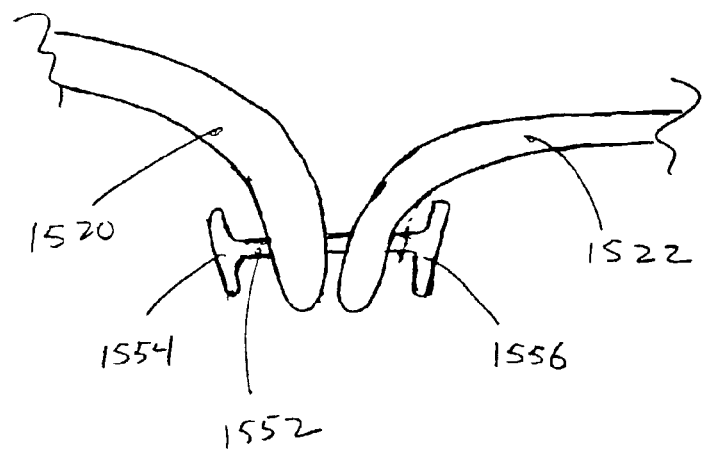
FIG. 15 illustrates one embodiment of a fastener holding mitral valve leaflets together.
Figure 18:
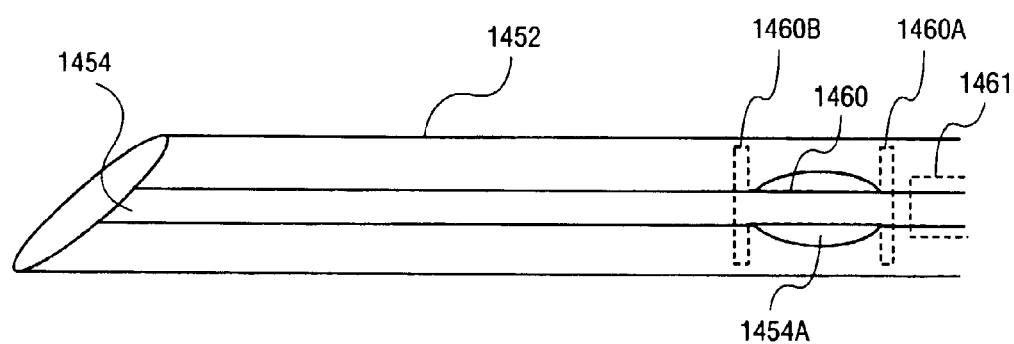
FIG. 18 shows a side view of a needle shown in FIG. 14.

FIG. 14 illustrates a leaflet fastener 1460 being ejected across mitral valve leaflets 1420, 1422. The embodiment shown in FIG. 14 may be understood as following the procedure described in FIG. 13. First and second stabilizers 1440, 1445 (extended from opening 1432 of catheter 1430) have relatively immobilized leaflets 1420, 1422 so that they are positioned relatively close to each other. Needle 1452 has extended from needle housing 1450 to penetrate through both leaflets 1420, 1422. Needle 1452 has a slot 1454 for ejecting fastener 1460. One end of fastener 1460 is shown being ejected from slot 1454 of needle 1452. As discussed above, a mandrel or push rod disposed within needle housing 1450 and extending through needle 1452 may be the mechanical method for ejecting fastener 1460. After ejecting one end of the fastener 1460 as shown in FIG. 14 through the wider portion of the slot 1454 (e.g., the wider portion of the slot 638 at the proximal end of slot 638 in FIG. 6), fastener 1460 may be advanced towards the distal tip of needle 1452 to release the opposite end of fastener 1460. Prior to ejecting the fastener 1460, the fastener 1460 is positioned in the slot 1454 as shown in FIG. 18. In particular, one end of 1460A of fastener 1460 is proximal to the wider portion 1454A of slot 1454, and on the other end 1460B of fastener 1460 is distal to this wider portion 1454A. A push rod 1461, shown in the view of FIG. 18, is proximal to the one end 1460A so that this one end 1460A may be pushed distally causing the one end 1460A to be ejected through the wider portion 1454A while the other end 1360B remains in the needle 1452. FIG. 15 illustrates fastener 1552 deployed across leaflets 1520, 1522 of a mitral valve. Ends 1554, 1556 of fastener 1552 hold the leaflets together. It may be appreciated by one of skill in the art that ends 1554, 1556 may be a variety of shapes that will hold the leaflets together, for example, disk-shaped or cylindrical-shaped.

Figure 16:
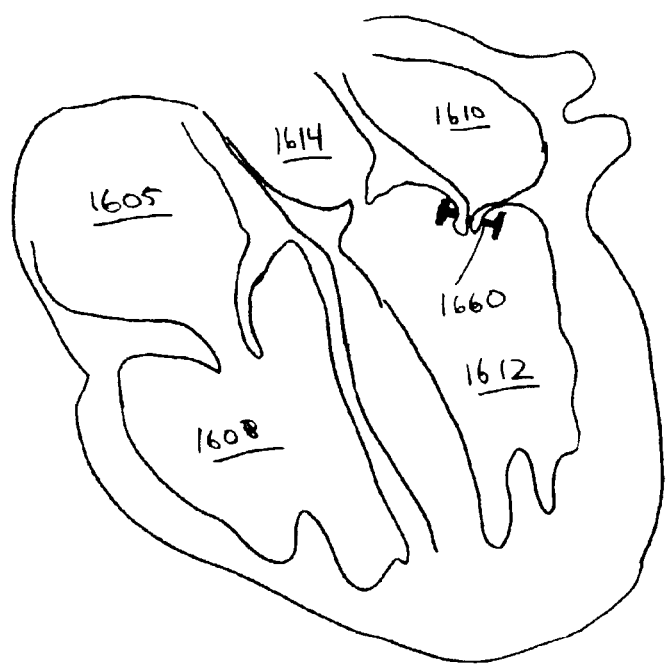
FIG. 16 illustrates cross-sectional view of a heart with a mitral valve fastener deployed therein.

FIG. 16 illustrates fastener 1660 deployed across the mitral valve leaflets with respect to the other regions of a heart (e.g., right atrium 1605, right ventricle 1608, left atrium 1610, left ventricle 1612, and aortic valve 1614). As shown, fastener 1660 may have a length that allows the leaflets some leeway to partially open or close. However, it may be appreciated that fastener 1660 may have a variety of lengths as deemed appropriate to treat mitral valve prolapse.

Figure 7:
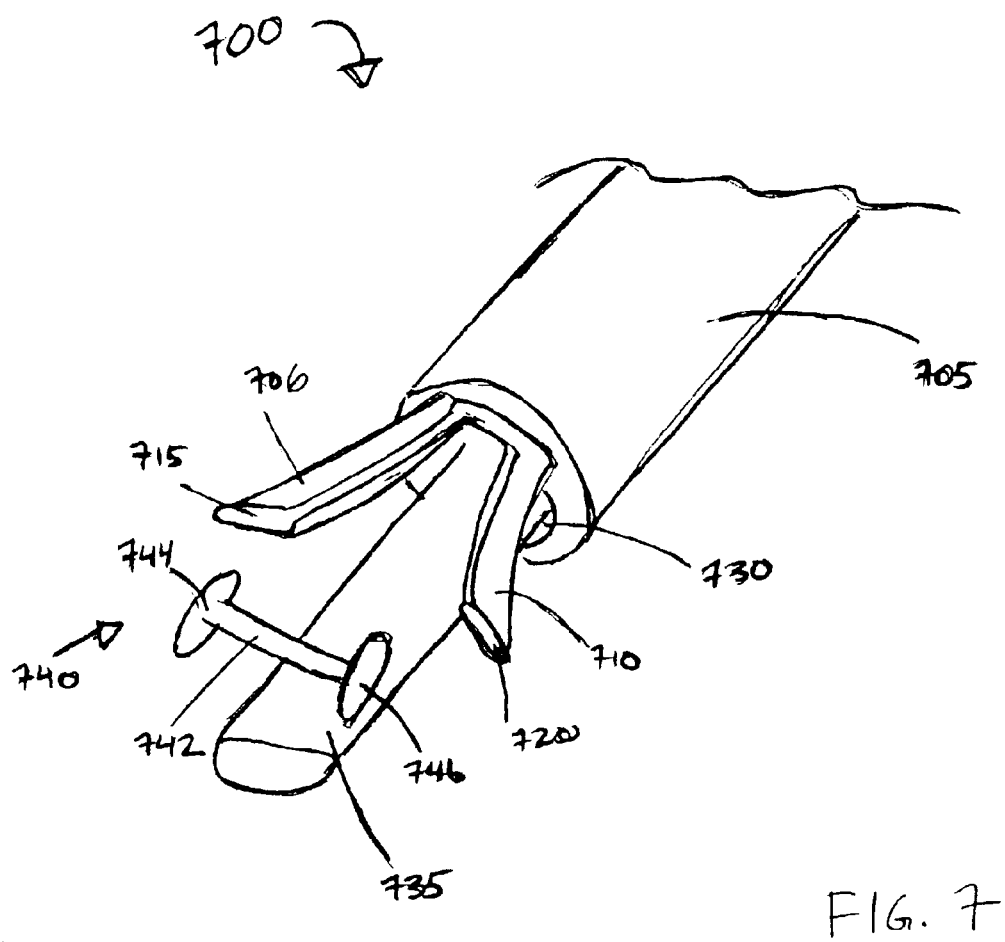
FIG. 7 illustrates one embodiment of a distal portion of a percutaneous medical device to treat a mitral valve.

FIG. 7 illustrates an alternative embodiment of a medical device to eject a fastener to treat the mitral valve. Distal portion 700 has an elongated catheter 705 in which a first needle 706 and a second needle 710 may extend from a distal end of catheter 705. It will be understood that the catheter 705 extends from this distal portion to a proximal portion which includes a control mechanism which is similar to the control mechanism 250 of FIG. 2. First needle 706 has a slot 715 along at least a portion of its longitudinal length towards the tip, and second needle 710 has a slot 720 also along at least a portion of its longitudinal length towards the tip. In one embodiment, first and second needles 706, 710 are flexible such that each needle may bend or flex toward a mitral valve leaflet and pull tendon, coupled near a distal end of one needle, may be used to cause a needle to bend, the pull tendon for each needle extends from near the distal end to a proximal control device which allows the pull tendon to be pulled prior to ejecting any portion of fastener 1460. Fastener 740 may be ejected from a first position within catheter 705 in which end 744 of fastener 740 is aligned within first needle 705, and end 746 of fastener 740 is aligned within second needle 710. By pushing the ends 744, 746 of fastener 740 through slots 715, 720 of first and second needles 706, 710, respectively, fastener 740 may be ejected from catheter 705. In one embodiment, a mandrel or push rod disposed within catheter 705 may be used to eject fastener 740 (e.g., a mandrel which is similar to mandrel 650 of FIG. 6). In one embodiment, each needle 706 and 710 has a mandrel or push rod which is used to push the fastener 740 out of the needle. Catheter 705 may also include a guidewire lumen 730 for inserting a guidewire 735. Guidewire 735 enables catheter 705 to advance percutaneously through a body vessel to the heart valve region. Described in greater detail below, first and second needles 706, 710 may each penetrate a mitral valve leaflet such that with the subsequent ejection of fastener 740, ends 744, 746 may hold the leaflets together. Fastener 740 is illustrated having disk-shaped ends 744, 746, but as discussed above, may have alternative shapes to hold leaflets together.

Figure 8:
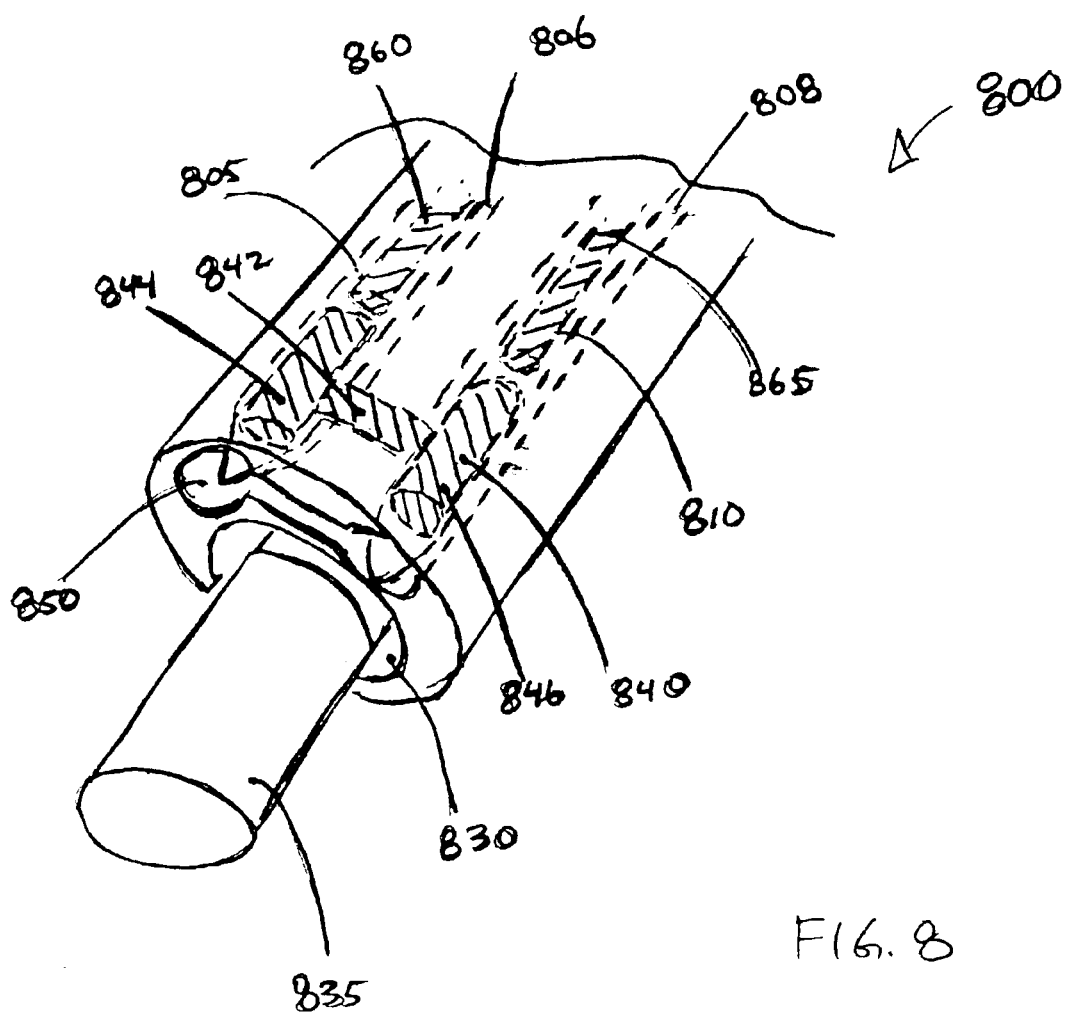
FIG. 8 illustrates an internal view of one embodiment of a distal portion of a percutaneous medical device to treat a mitral valve.

FIG. 8 illustrates a partial, internal view 800 of a fastener retracted and housed within a distal portion of a catheter corresponding to a medical device (e.g., the medical device shown in and discussed with respect to FIG. 7) to treat a mitral valve. Guidewire lumen 830 contains guidewire 835. First and second needles 805, 810 are housed within needle lumens 806, 808, respectively. End 844 (having a cylindrical shape) of fastener 840 is disposed within a slot of first needle 805, and end 846 of fastener 840 is disposed within a slot of second needle 810. Opening 850 of the distal end of the catheter shown in FIG. 8 is shaped substantially similar to fastener 840 such that first and second needles 805, 810 may extend out from catheter 805 with fastener 840 disposed within the needles. This feature can also be seen in the end view of the distal end of the catheter shown in FIG. 9. Mandrels 860, 865 may be disposed proximal to ends 844, 846 of fastener in this loaded position. By advancing mandrels 860, 865, fastener 840 may be ejected from needles 805, 810.

Figure 9:
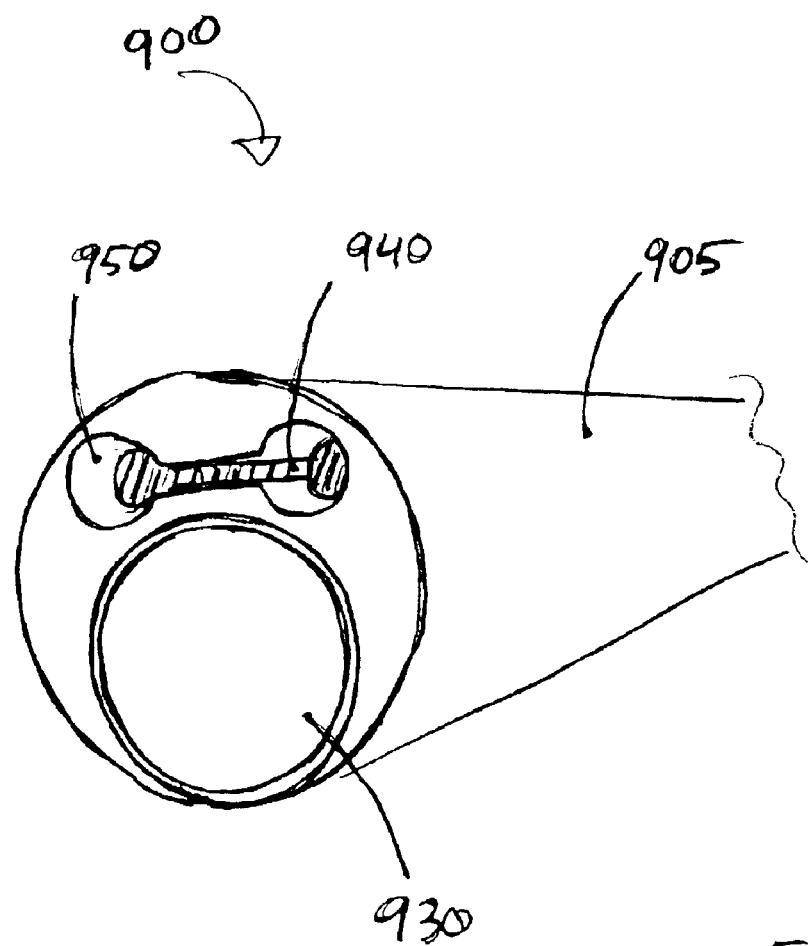
FIG. 9 illustrates a distal end view of one embodiment of a percutaneous medical device to treat a mitral valve.

FIG. 9 illustrates one embodiment of an end view of a distal portion 900 of the medical device of FIG. 8. In this embodiment, fastener 940 is loaded and in a retracted position within catheter 905. Catheter 905 includes a guidewire lumen 930 for inserting a guidewire (e.g., guidewire 835) which is used to position the distal end of the catheter relative to the mistral valve. Opening 950 of catheter 905 is shaped substantially similar to fastener 940 and needles (e.g., first and second needles 805, 810) for extending the needles out of the distal end of the catheter 905 while the needles still include the fastener 940 and ejecting fastener 940.

Figure 17:
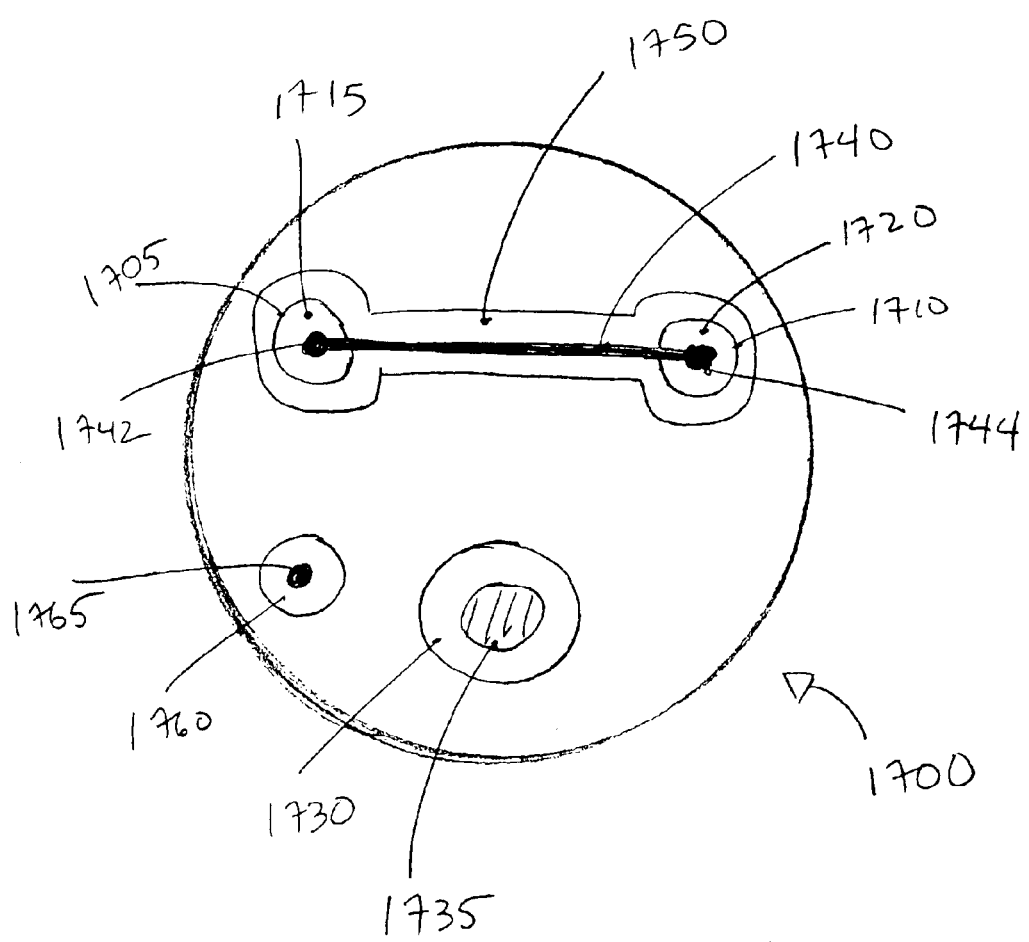
FIG. 17 illustrates another cross-sectional view of one embodiment of a distal portion of a percutaneous medical device to treat a mitral valve.

FIG. 17 illustrates a cross-sectional view of a distal portion of the medical device (e.g., portions 700 and 800 discussed above). A guidewire lumen 1730 may be formed within catheter 1700 in which a guidewire 1735 may be disposed therein. Lumen 1750 formed within catheter 1700 contains first and second needles 1705, 1710. Needle lumen 1715 of needle 1705 and needle lumen 1720 of needle 1710 respectively contain the ends 1742, 1744 of fastener 1740. Catheter 1700 may also have lumen 1760 formed therein to contain wire 1765 (a pull tendon) for steering capability. The guidewire 1735 extends from near the distal end to a proximal region from where the insertion of the guidewire is controlled. The needles 1705 and 1710 extend from the distal end to a proximal region where a control mechanism (e.g., similar to control mechanism 250 in FIG. 2) is couples to the needles to control the extension and retraction of the needles. Mandrels or push rods in the lumens of needles 1705 and 1710 are used to push the fastener 1750 out of the distal end of catheter 1700, and these mandrels or push rods extend from near the distal end to a proximal region where they are coupled to a control mechanism (e.g., similar to control mechanism 250 in FIG. 2) which allows for control of the extension (and retraction) of the mandrels or push rods to push the fastener 1750. The wire 1765 extends from near the distal end of the catheter 1700 to a proximal region where the wire 1765 is coupled to a control mechanism (e.g., similar to control mechanism 250) which allows for steering of the distal portion of catheter 1700. Also, in certain embodiments, the needles 1705 and 1710 each include a pull tendon, attached near a distal end of each needle, which allows a user to control bending and flexing of each needle by pulling the respective pull tendon through a proximal end of the pull tendon. In an alternative embodiment, the ends of needles 1705 and 1710 may be formed from a memory shape material (e.g., nickel titanium) which has one shape (e.g., straight but flexible) at one temperature and another shape (e.g., a flexed curve) at another temperature.

Figure 10A:
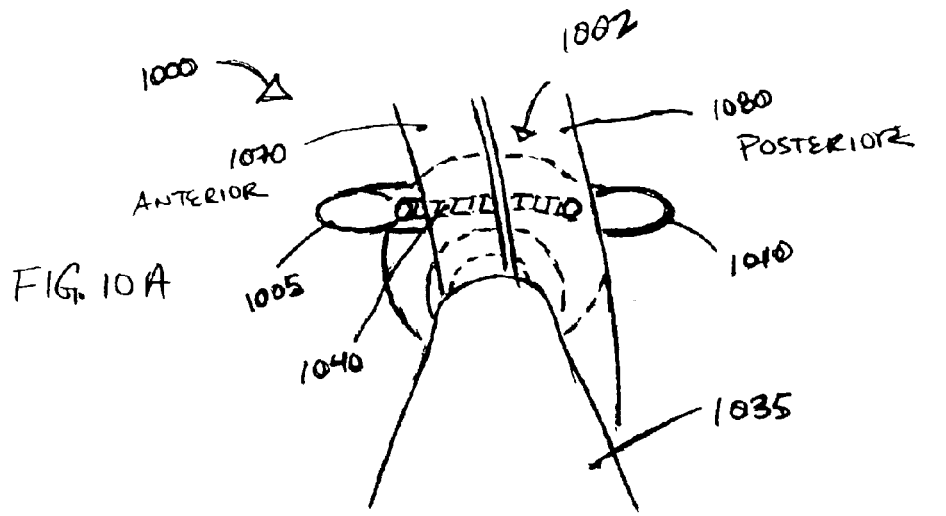
FIGS. 10A–10C illustrate one exemplary method of ejecting a mitral valve fastener.
Figure 10B:
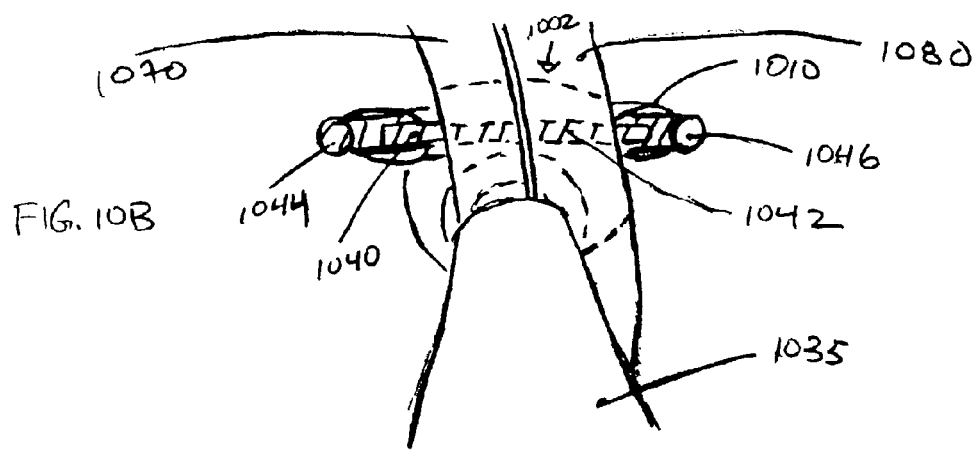
Figure 10C:
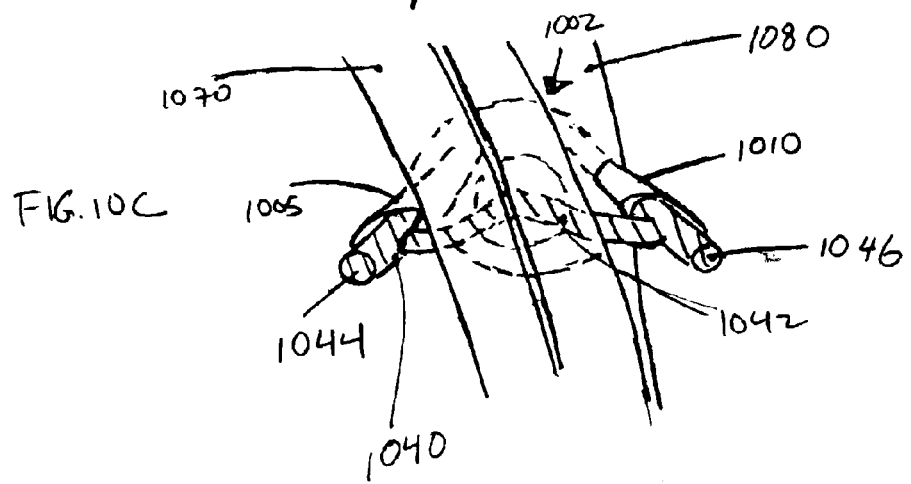

FIGS. 10A–10C illustrate one exemplary embodiment of a method for ejecting a fastener to bind two leaflets of a mitral valve. Medical device 1000 (e.g., leaflet fastener delivery system such as those systems shown in FIGS. 7–9 and 17) illustrated in FIG. 10A may be advanced percutaneously to the mitral valve by first passing a guide wire 1035 across the mitral valve, from the atrium to the left ventricle. The views of FIGS. 10A–10C look up from the left ventricle at the mitral valve. The guidewire is advanced in an antegrade manner to the mitral valve region percutaneously, entering, for example, through the femoral artery to the right atrium, and puncturing through the septum between the right and left atria and then entering into the left atrium and passing through and across the mitral valve. An obturator may also be used (similar to those used in the current practice of balloon valvioplasty). Percutaneous methods for advancing a guidewire to the mitral valve region and accessing the mitral valve across the septum is known in the art; accordingly, a detailed description is not provided. Various imaging techniques known in the art may also be used to locate the mitral valve leaflets. For example, echo imaging, infrared illumination, x-ray, and magnetic resonance imaging methods may be utilized. These imaging techniques are known in the art; accordingly, a detailed description is not provided. Medical device 1000 is placed over guide wire 1035 and into the body through an introducer (a known device in the art) in a vein. A guide catheter (not shown) may first be placed over guide wire 1035 and advanced through the introducer into a vessel lumen. The guide catheter may also contain its own guide wire component to provide the catheter with the ability to steer its way to the target location. As an alternative to an over-the-wire catheter, a rapid exchange catheter delivery system may be utilized. As such, the catheter may be any of the catheter types used in the art, including but not limited to "rapid exchange" (RX) catheters, "over-the-wire" (OTW) catheters, or a "tip RX" catheters. Guide wire 1035 and guide catheter may be advanced through the vein to the vena cava and into the right atrium of the heart. In an alternative embodiment, the guide catheter may be used to provide extra support to medical device 1000.

Medical device 1000 may then be advanced to the mitral valve over guide wire 1035 and placed across the mitral valve from the left atrium. As shown in FIG. 10A, the distal portion 1002 of medical device 1000 is placed in the left atrium just above the tips of the anterior 1070 and posterior 1080 mitral valve leaflets and the guidewire 1035 extends from the distal end of device 1000 through the mitral valve and into the left ventricle. A proximal portion of medical device 1000 may have a handle and control mechanism (e.g., similar to control mechanism 250 of FIG. 2) with actuating knob 260 which may be used to extend the first needle 1005A and second needle 1010 out of distal end 1002 and across and through anterior 1070 and posterior 1080 mitral valve leaflets. In this position, first and second needles 1005, 1010 sandwich anterior 1070 and posterior 1080 mitral valve leaflets. Fastener 1040, preloaded with each end disposed within first needle 1005 and second needle 1010, has not been ejected. In one embodiment, first and second needles 1005 and 1010 are flexible. As illustrated, because guidewire 1035 passes through an opening between the mitral valve leaflets, first needle 1005 may bend towards anterior leaflet 1070 and second needle 1010 may bend towards leaflet 1080, puncturing through the leaflets from the left atrium side to the left ventricle side.

Next, as illustrated by FIG. 10B, fastener 1040 may be advanced towards the distal tips of first and second needles 1005 and 1010. Ends 1044 and 1046 of fastener 1040 are shown partially extending from the needle tips. In one embodiment of fastener 1040, ends 1044 and 1046 are connected to each other by elongated central portion 1042. In one embodiment, fastener 1040 may be advanced towards the needle tips by a mandrel (e.g., mandrels 860, 865) disposed within catheter tip 1002 and controlled by a control mechanism which is similar to control mechanism 250 described above. FIG. 10C illustrates fastener 1040 that has been ejected from first needle 1005 and second needle 1010. When ejected to bind anterior leaflet 1070 and posterior leaflet 1080, ends 1044, 1046 of fastener 1040 are disposed on opposite sides of each other, with both leaflets between them. In this manner, the movement and separation of anterior leaflet 1070 and posterior leaflet is restricted. Once fastener 1040 has been ejected, first and second needles 1005 and 1010 may be retracted back into distal portion 1002 and medical device 1000 may be removed percutaneously from the mitral valve region and from the patient's vasculature. The embodiments and methods described with respect to FIGS. 7–10C do not have stabilizers (e.g., stabilizers 325, 330 of FIG. 3). Stabilizers may not be necessary because first and second needles 1005 and 1010 each penetrate through a leaflet of the mitral valve, thereby stabilizing them so that fastener 1040A may be ejected through them. For example, needles 1005 and 1010 may be extended from distal portion 1002 when the mitral valve leaflets converge toward each other during systole.

Figure 11A:
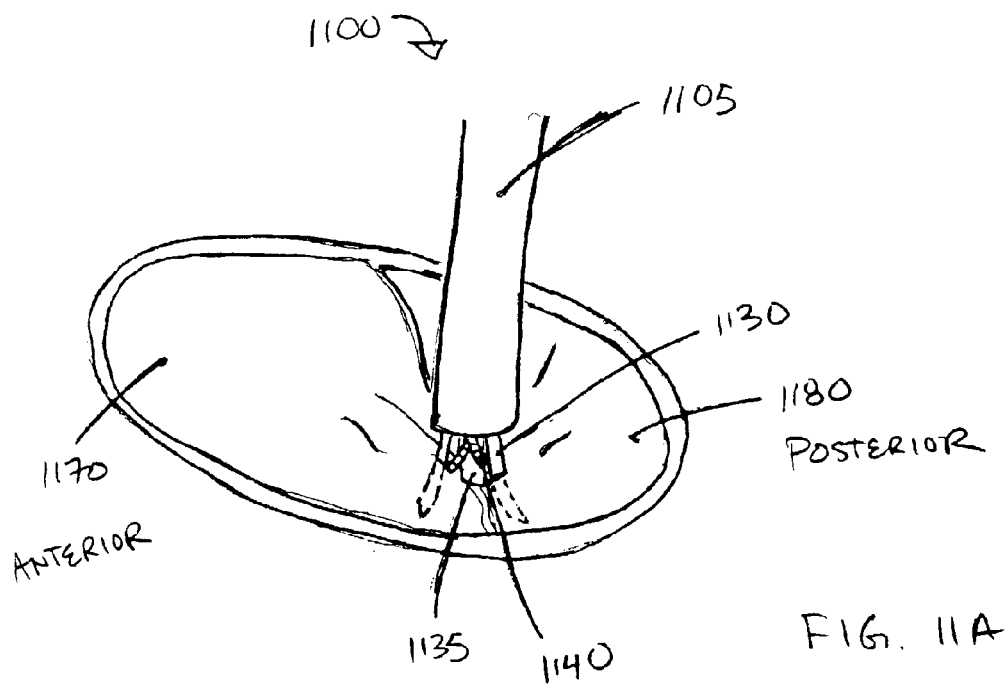
FIGS. 11A–11D illustrate another exemplary method of ejecting a mitral valve fastener.

FIGS. 11A–11D illustrate another view of an exemplary embodiment for ejecting a mitral valve leaflet fastener. As shown by FIG. 11A, medical device 1100 has a distal portion 1105 of an elongated catheter approaching anterior 1170 and posterior 1180 leaflets of a mitral valve down from the left atrium (described above). Guidewire 1135 may extend through the leaflets to position distal portion 1105 properly between anterior 1170 and posterior 1180 leaflets. First and second needles 1125, 1130 have extended from distal portion 1105 and penetrated through each leaflet (e.g., first needle 1125 through anterior leaflet 1170 and second needle 1130 through posterior leaflet 1180). Fastener 1140 is shown being ejected from first and second needles 1125 and 1130. In one embodiment, fastener 1140 may be ejected by the method described above with respect to FIGS. 10A–10C.

Figure 11B:
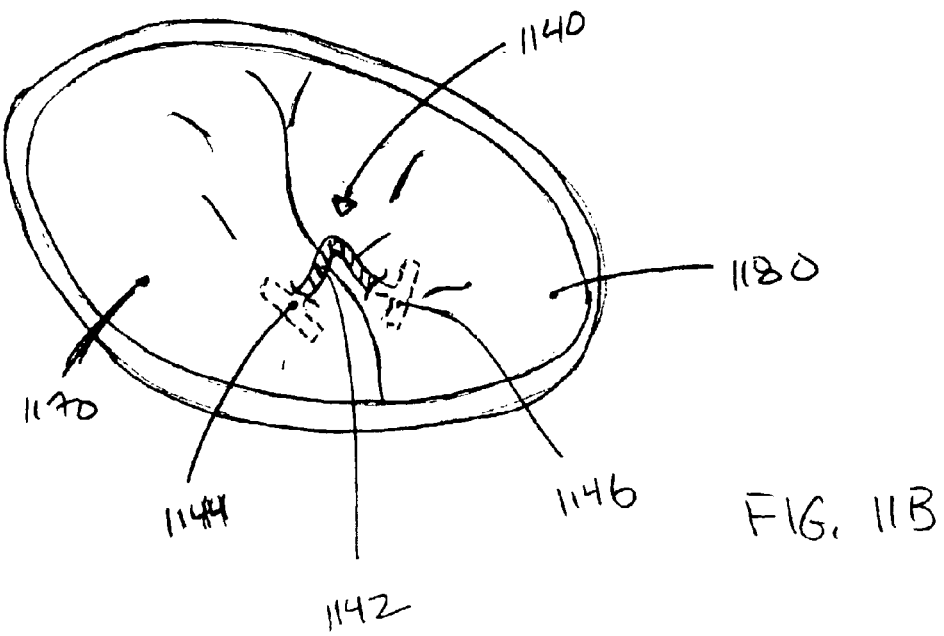

FIG. 11B illustrates fastener 1140 ejected to bind anterior 1170 and posterior 1180 leaflets together. Catheter 1105 has been removed from the mitral valve region. In one embodiment, fastener 1140 has an elongated central portion 1142 with cylindrical-shaped ends 1144 and 1146. Elongated central portion 1142 is disposed substantially on the atrial side of the mitral valve while ends 1144 and 1146 are disposed on the ventricle side of the mitral valve. Ends 1144 and 1146 are structured such that they are substantially perpendicular to elongated central portion 1142 to prevent ends 1144 and 1146 from passing back from the ventricle side to the atrial side of the mitral valve. As discussed above, ends 1144 and 1146, in alternative embodiments, may have other shapes (e.g., disk-shaped, a combination of disk and cylinder shapes) to prevent them from inadvertently passing from the ventricle side to the atrial side.

Figure 11C:
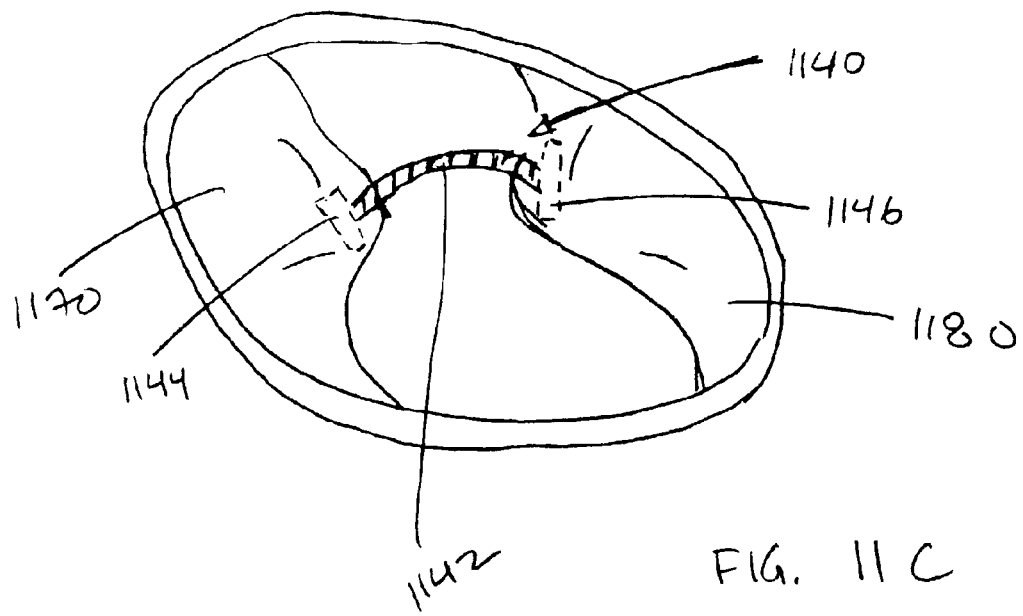
Figure 11D:
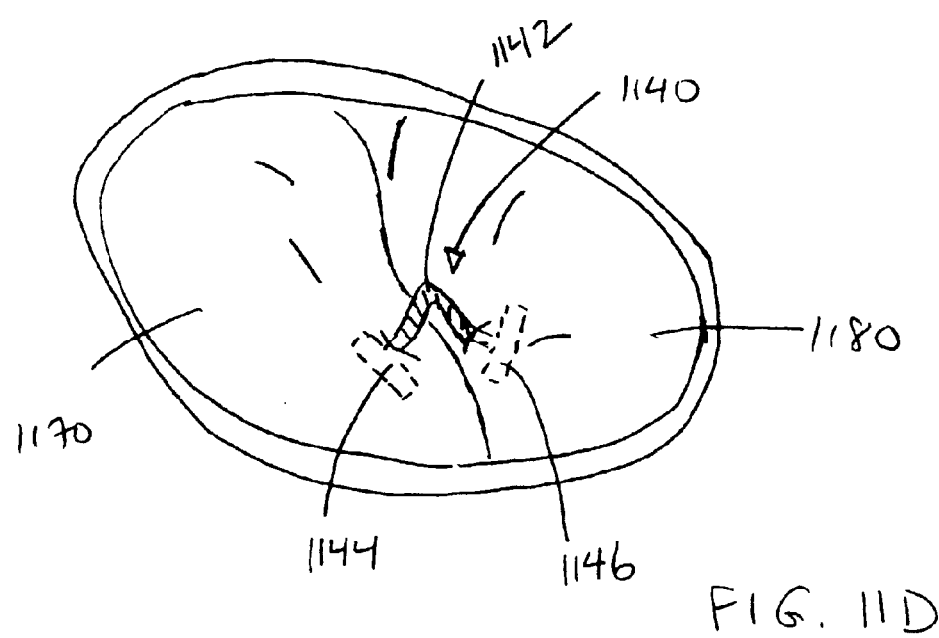

FIG. 11C illustrates one embodiment of the behavior of fastener 1140 during diastole, when the anterior 1170 and posterior 1180 leaflets open. Fastener 1140 (including elongated central portion 1142 and ends 1144, 1146) may be made of various biocompatible polymers that exhibit flexible or compliant properties. As such, the elongated central portion 1142 may stretch to allow the area between the leaflets that are bound together to separate and allow oxygenated blood to flow down into the left ventricle. The elastic properties of fastener 1140 provide an advantage over rigid fasteners that form a "FIG. 8" like shape with the anterior 1170 and posterior 1180 leaflets during diastole to allow blood flow into the left ventricle. When the mitral valve closes, as illustrated by FIG. 11D, the resilient properties of fastener 1140 force the leaflets toward each other to form a coapting surface.

In one embodiment, a fastener (e.g., fastener 1140) percutaneously placed near a mitral valve region, or a device placed in the coronary sinus to treat the mitral valve, may be used to deliver or release a drug or therapeutic agent to treat mitral valve regurgitation. Various drugs are known in the art for treating mitral valve regurgitation. For example, administering nitroprusside (a vascular smooth muscle relaxant) may effectively diminish the amount of mitral regurgitation, thereby increasing forward output by the left ventricle and reducing pulmonary congestion. Inotropic agents such as dobutamine may also be administered to increase the force of contraction of the myocardium. In one embodiment, a percutaneous medical device to treat mitral valve regurgitation, such as leaflet fastener, a support annulus for resizing a mitral valve annulus, clips to ligate the mitral valve leaflets, or a device placed in the coronary sinus near the mitral valve region, may be coated with these exemplary drugs for delivery near the mitral valve region. The drugs may have timed-release features to be released slowly over a certain period of time. The drug eluting fastener, support annulus, or other devices may also have the drug or agent dispersed on the surface of the support annulus or other devices, or co-dissolved in a matrix solution to be dispersed on the support annulus. Methods to coat the support annulus with a therapeutic drug include dip coating, spin coating, spray coating, or other coating methods commonly practiced in the art.

In some cases, patients with defective heart valves may have concomitant coronary artery disease (CAD). As such, it may be advantageous for a support annulus to deliver a drug to treat occlusions in the artery or other related CAD such as vulnerable plaque. The drug to treat CAD may be delivered alone or in combination with drugs to treat mitral valve regurgitation. Drugs to treat CAD include, but are not limited to, statins, lipid lowering agents, antioxidants, extracellular matrix synthesis promoters, inhibitors of plaque inflammation and extracellular degradation, estradiol drug classes and its derivatives.

In one embodiment, the drugs to treat CAD may be coated on a leaflet fastener, support annulus, or other device using methods such as dip coating, spin coating, spray coating or other coating methods known in the art. The drug may alternatively be encapsulated in microparticles or nanoparticles and dispersed in a coating on the support annulus or other device. A diffusion limiting top-coat may optionally be applied to the above coatings. The active agents may optionally be loaded on a support annulus or other device together either by adding them together to the solution of the matrix polymer before coating, or by coating different layers, each containing a different agent or combination of agents. The drug eluting fastener, support annulus, or other device may alternatively have an active agent or a combination of agents dispersed in a bioerodable annulus forming polymer.

In the foregoing specification, a medical device has been described with reference to specific exemplary embodiments thereof. For example, the medical device may be used to treat valves other than the mitral valve. It will, however, be evident that various modifications and changes may be made thereto without departing from the broader spirit and scope of the medical device as set forth in the appended claims. The specification and figures are, accordingly, to be regarded in an illustrative rather than a restrictive sense.

What is claimed is:

1. A medical device, comprising:
   an elongated catheter having a proximal portion and a distal portion;
   at least one needle disposed within said elongated catheter, said at least one needle having a slot formed along a needle length with a first opening and a second opening; and
   a fastener ejectable from said at least one needle, wherein said fastener includes a first end and a second end, said first end capable of ejecting from said first opening and said second end capable of ejecting from said second opening to fasten a body tissue pierced by said at least one needle.

2. The medical device of claim 1, further comprising at least one stabilizer deployable from said distal portion of said elongated catheter, wherein said at least one stabilizer is adapted to restrict a movement of said body tissue.

3. The medical device of claim 1, wherein said fastener has an elongated central portion with said first end and said second end, and when ejected from said at least one needle, holds said body tissue between said first and second ends.

4. The medical device of claim 3, wherein said body tissue comprises at least one mitral valve leaflet.

5. The medical device of claim 4, wherein said catheter is adapted for percutaneous advancement to said at least one mitral valve leaflet.

6. The medical device of claim 3, wherein said fastener is flexible.

7. The medical device of claim 5, further comprising a mandrel disposed within said at least one needle, wherein said mandrel ejects said fastener.

8. The medical device of claim 7, wherein said elongated catheter further comprises a guidewire lumen.

9. The medical device of claim 7, wherein said elongated catheter further comprising a control mechanism disposed near said proximal portion of said elongated catheter.

10. The medical device of claim 1, wherein said elongated catheter is steerable.

11. A percutaneous mitral valve device, comprising:
    a catheter having a proximal portion, a steerable distal portion, and a portion adapted to be disposed through an aortic valve;
    at least one needle extendable from said distal portion, said at least one needle having a slot formed along an elongated central portion with a first opening and a second opening; and
    a fastener ejectable from said at least one needle, wherein said fastener includes a first end and a second end, said first end capable of ejecting from said first opening and said second end capable of ejecting from said second opening to fasten a first mitral valve leaflet to a second mitral valve leaflet.

12. The percutaneous mitral valve device of claim 11, wherein said fastener holds said first leaflet and said second leaflet between said first end and said second end.

13. The percutaneous mitral valve device of claim 12, further comprising a mandrel disposed within said at least one needle, wherein said mandrel ejects said fastener.

14. The percutaneous mitral valve device of claim 13, further comprising a guidewire lumen formed within said catheter, and a first stabilizer extendable from said distal portion and adapted to hold said first mitral valve leaflet, and a second stabilizer extendable from said distal portion and adapted to hold said second mitral valve leaflet.

15. The percutaneous mitral valve device of claim 12, wherein said fastener is made of a polymer.

16. The percutaneous mitral valve device of claim 12, wherein said fastener is made of a biodegradable material.

17. The percutaneous mitral valve device of claim 12, wherein said fastener is made of a metallic material.

18. The percutaneous mitral valve device of claim 12, wherein said fastener is made of a flexible material.

19. A percutaneous mitral valve device, comprising:
    a catheter having a proximal portion and a steerable distal portion;

a first stabilizer extendable from said distal portion, said first stabilizer adapted to hold a first mitral valve leaflet;

a second stabilizer extendable from said distal portion, said second stabilizer adapted to hold said second a second mitral valve leaflet;

a needle extendable from said distal portion, said needle having a slot formed along a needle length with a first opening and a second opening; and a fastener ejectable from said first needle, wherein said fastener includes a first end and a second end, said first end capable of ejecting from said first opening and said second end capable of ejecting from said second opening to fasten said first mitral valve leaflet to said second mitral valve leaflet.

20. The percutaneous mitral valve device of claim 19, wherein said fastener has an elongated central portion with said first end and said second end, and when ejected from said first needle, holds said first leaflet and said second leaflet between said first end and said second end.

21. The percutaneous mitral valve device of claim 20, further comprising a mandrel disposed within said needle, wherein said mandrel ejects said fastener.

22. The percutaneous mitral valve device of claim 21, further comprising a guidewire lumen formed within said catheter.

23. The percutaneous mitral valve device of claim 20, wherein said fastener is made of a polymer.

24. The percutaneous mitral valve device of claim 20, wherein said fastener is made of a biodegradable material.

25. The percutaneous mitral valve device of claim 20, wherein said fastener is made of a metallic material.

26. The percutaneous mitral valve device of claim 22, further comprising a control mechanism disposed near said proximal portion of said elongated catheter.

27. The percutaneous mitral valve device of claim 20, wherein said first end and said second end of said fastener are disk-shaped.

28. The percutaneous mitral valve device of claim 20, wherein said first end and said second end of said fastener are cylindrical-shaped.

29. A percutaneous mitral valve device, comprising:
a catheter having a proximal portion and a steerable distal portion;
a first needle extendable from a housing disposed near said distal portion;
a second needle extendable from said distal portion housing, wherein said housing forms a lumen extending into a first opening for said first needle and a second opening for said second needle, said lumen having a central portion extending between said first opening and said second opening; and
a fastener having a first end capable of ejecting from said first needle and a second end capable of ejecting from said second needle, wherein said first needle is adapted to penetrate a first mitral valve leaflet and said second needle is adapted to penetrate said second mitral valve leaflet, and wherein said fastener, having a nonadjustable length, fastens said first mitral valve leaflet to said second mitral valve leaflet.

30. The percutaneous mitral valve device of claim 29, wherein said fastener has an elongated central portion with said first end and said second end, and when ejected from said first and second needles, holds said first leaflet and said second leaflet between said first and said second ends.

31. The percutaneous mitral valve device of claim 30, further comprising a mandrel disposed within said needle, wherein said mandrel ejects said fastener.

32. The percutaneous mitral valve device of claim 31, further comprising a guidewire lumen formed within said catheter.

33. The percutaneous mitral valve device of claim 32, further comprising a control mechanism disposed near said proximal portion of said elongated catheter.

34. The percutaneous mitral valve device of claim 30, wherein said fastener is made of a polymer.

35. The percutaneous mitral valve device of claim 30, wherein said fastener is made of a biodegradable material.

36. The percutaneous mitral valve device of claim 30, wherein said fastener is made of a metallic material.

37. The percutaneous mitral valve device of claim 30, wherein said first end and said second end of said fastener are disk-shaped.

38. The percutaneous mitral valve device of claim 30, wherein said first end and said second end of said fastener are cylindrical-shaped.

39. The percutaneous mitral valve device of claim 29, wherein said first and said second needles are flexible.

40. A method of treating a mitral valve, the method comprising:
locating said mitral valve percutaneously;
ejecting a first end of a fastener from a first slot of a needle through a first leaflet of said mitral valve; and
ejecting a second end of a fastener from a second slot of said needle through a second leaflet of said mitral valve.

41. The method of claim 40, wherein locating further comprises advancing a steerable catheter having said fastener to said mitral valve.

42. The method of claim 41, wherein locating further comprises stabilizing a first and a second leaflet of said mitral valve to restrict a movement of said first and said second leaflets.

43. The method of claim 42, wherein ejecting further comprises penetrating said needle through said first and said leaflets.

44. The method of claim 43, wherein ejecting further comprises releasing said said first end and said second end simultaneously.

45. The method of claim 41, wherein locating further comprises advancing a medical device across a septum and into the left atrium of a heart.

46. The method of claim 40, wherein ejecting further comprises:
piercing said first leaflet with a first needle and second leaflet with a second needle; and
releasing said fastener from said first and second needles.

47. The method of claim 46, wherein releasing comprises advancing a mandrel disposed within said first and second needles.

48. A medical device to treat a mitral valve, comprising:
means for locating said mitral valve percutaneously;
means for ejecting a first end of a fastener from a first slot of a needle through a first leaflet of said mitral valve; and
means for ejecting a second end of said fastener from a second slot of said needle through a second leaflet of said mitral valve.

49. The medical device of claim 48, wherein means for locating further comprises means for advancing a steerable catheter having said fastener to said mitral valve.

50. The medical device of claim 49, wherein means for locating further comprises means for stabilizing a first and a second leaflet of said mitral valve to restrict a movement of said first and said second leaflets.

51. The medical device of claim 50, wherein means for ejecting further comprises means for penetrating a needle through said first and said leaflets.

52. The medical device of claim 51, wherein means for ejecting further comprises means for releasing said fastener from said needle.

53. The medical device of claim 49, wherein means for locating further comprises means for advancing a medical device across a septum and into the left atrium of a heart.

54. The medical device of claim 48, wherein means for ejecting further comprises:

means for piercing said first leaflet with a first needle and second leaflet with a second needle; and means for releasing said fastener from said first and second needles.

55. The medical device of claim 54, wherein means for releasing comprises means for advancing a mandrel disposed within said first and second needles.

* * * * *